(12) United States Patent
Chung

(10) Patent No.: US 11,944,640 B2
(45) Date of Patent: *Apr. 2, 2024

(54) ZINC-[GAMMA]-PGA COMPOSITIONS AND METHODS FOR TREATING CANCER

(71) Applicant: XYLONIX PTE. LTD., Singapore (SG)

(72) Inventor: Jinhyuk Fred Chung, Singapore (SG)

(73) Assignee: XYLONIX PTE. LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/346,286

(22) PCT Filed: Oct. 31, 2017

(86) PCT No.: PCT/SG2017/050545
§ 371 (c)(1),
(2) Date: Apr. 30, 2019

(87) PCT Pub. No.: WO2018/084806
PCT Pub. Date: May 11, 2018

(65) Prior Publication Data
US 2019/0255104 A1    Aug. 22, 2019

(30) Foreign Application Priority Data
Nov. 1, 2016 (SG) .................. 10201609131Y

(51) Int. Cl.
| | | |
|---|---|---|
| *A61K 9/70* | (2006.01) | |
| *A24D 1/02* | (2006.01) | |
| *A61K 33/30* | (2006.01) | |
| *A61K 33/44* | (2006.01) | |
| *A61K 38/02* | (2006.01) | |
| *A61K 47/54* | (2017.01) | |
| *A61K 47/55* | (2017.01) | |
| *A61K 47/62* | (2017.01) | |
| *A61K 47/64* | (2017.01) | |
| *A61M 15/06* | (2006.01) | |
| *A61P 35/00* | (2006.01) | |
| *C01B 32/156* | (2017.01) | |
| *D21H 27/00* | (2006.01) | |
| *A61K 31/20* | (2006.01) | |
| *A61K 33/243* | (2019.01) | |
| *D21H 19/38* | (2006.01) | |

(52) U.S. Cl.
CPC .............. *A61K 33/30* (2013.01); *A61K 38/02* (2013.01); *A61K 47/542* (2017.08); *A61K 47/551* (2017.08); *A61K 47/62* (2017.08); *A61K 47/645* (2017.08); *A61P 35/00* (2018.01)

(58) Field of Classification Search
CPC ...... A61K 33/30; A61K 47/62; A61K 47/542; A61K 47/645; A61K 47/551; A61K 38/02; A61P 35/00
See application file for complete search history.

(56) References Cited

U.S. PATENT DOCUMENTS

| | | |
|---|---|---|
| 2,897,122 A | 7/1959 | Millar et al. |
| 5,447,732 A | 9/1995 | Tanimoto et al. |
| 7,528,125 B2 | 5/2009 | Magda et al. |
| 9,636,411 B2 | 5/2017 | Bai |
| 2001/0034363 A1 | 10/2001 | Li et al. |
| 2002/0040029 A1 | 4/2002 | Bowen |
| 2002/0061599 A1 | 5/2002 | Elling |
| 2005/0038071 A1 | 2/2005 | Bowen |
| 2005/0100593 A1 | 5/2005 | Furuta |
| 2005/0261320 A1 | 11/2005 | Chu |
| 2008/0253969 A1 | 10/2008 | Lei et al. |
| 2008/0279778 A1 | 11/2008 | Van et al. |
| 2008/0280974 A1 | 11/2008 | Weingarten et al. |
| 2008/0292687 A1 | 11/2008 | Cheng |
| 2011/0117210 A1 | 5/2011 | Ugolkov |
| 2016/0030454 A1 | 2/2016 | Bent |

(Continued)

FOREIGN PATENT DOCUMENTS

| | | |
|---|---|---|
| CN | 101716180 | 6/2010 |
| EP | 0605757 A1 | 7/1994 |

(Continued)

OTHER PUBLICATIONS

Subarna Karmaker, Tapan K. Saha, Yutaka Yoshikawa, Hiromu Sakurai, Macromol. Biosci. 2009, 9, 279-286 (Year: 2009).*
Bae, Hee Ho, Mi Young Cho, Ji Hyeon Hong, Haryoung Poo, Moon-Hee Sung, and Yong Taik Lim (Year: 2012).*
Duan et al. Small 2015, 11, No. 32, 3962-3972 (Year: 2015).*
Mignani et al. Biomacromolecules 16, 1 (2015): 1-27 (Year: 2015).*
Cirone et al. OncoImmunology 2:9, e26198, Sep. 2013 (Year: 2013).*
Rank et al. Nucleic Acids Research, vol. 44, Issue 21, 10386-10405, Published online Sep. 2016 (Year: 2016).*

(Continued)

*Primary Examiner* — Mina Haghighatian
*Assistant Examiner* — Janice Y Silverman
(74) *Attorney, Agent, or Firm* — White & Case LLP

(57) ABSTRACT

The invention relates to pharmaceutical compositions comprising a $zinc^{2+}$ salt and a γ-polyglutamic acid carrier, and, optionally, an NF-kB inhibitor as a tumor-sensitizing agent, and methods for using such compositions to treat tumors in patients. Methods include administering a liquid dosage form or a solid dosage form of a therapeutically effective amount of a Zn(II) salt and a γ-polyglutamic acid carrier to a patient in need thereof. Methods of treating a broad spectrum of human tumors, including tumors with a drug-resistant phenotype, using the disclosed compositions are provided. Tumors that respond to the pharmaceutical compositions disclosed herein include neuroendocrine (neuroblastoma), gastric, uterine, and lung tumors.

6 Claims, 5 Drawing Sheets

(56) References Cited

U.S. PATENT DOCUMENTS

| | | | |
|---|---|---|---|
| 2016/0122739 A1 | 5/2016 | Sheehan | |
| 2016/0151333 A1 | 6/2016 | Ketter et al. | |

FOREIGN PATENT DOCUMENTS

| | | |
|---|---|---|
| EP | 3006045 B1 | 4/2017 |
| IT | MI950515 | 9/1996 |
| JP | H0330648 A | 2/1991 |
| JP | 2712583 B2 | 2/1998 |
| JP | H11-313618 A | 11/1999 |
| JP | 2001204441 A | 7/2001 |
| JP | 2006-045216 A | 2/2006 |
| JP | 2016069303 A | 5/2016 |
| KR | 10-2005-0006910 A | 1/2005 |
| SG | 10201609131 Y | 11/2016 |
| SG | 10201708886 R | 10/2017 |
| WO | WO-2004080210 | 9/2004 |
| WO | WO-2007043606 | 4/2007 |
| WO | WO-2010/117370 A1 | 10/2010 |
| WO | WO-2010/134965 A1 | 11/2010 |
| WO | WO-2011110930 A2 | 9/2011 |
| WO | WO-2013/039488 A1 | 3/2013 |
| WO | WO-2014/081563 A1 | 5/2014 |
| WO | WO-2014133196 A1 | 9/2014 |
| WO | WO-2014155142 | 10/2014 |
| WO | WO-2016/057744 A1 | 4/2016 |
| WO | WO-2016088816 A1 | 6/2016 |
| WO | WO-2018035395 | 2/2018 |
| WO | WO-2018084806 | 5/2018 |
| WO | WO-2019245458 A1 | 12/2019 |

OTHER PUBLICATIONS

Alsaheb et al. (Der Pharmacia Lettre, 2016, 8 (9):217-225 (Year: 2016).*

Zinc Pyrithione from Cameo Chemicals: web page <https://cameochemicals.noaa.gov/chemical/21240l>, Dec. 13, 2016, retrieved from Internet Archive Wayback Machine <https://web.archive.org/web/20161213183937/https://cameochemicals.noaa.gov/chemical/21240> on Feb. 2, 2021 (Year: 2016).*

Feng, Zhen, et al. "Poly (γ,L-glutamic acid)-cisplatin bioconjugate exhibits potent antitumor activity with low toxicity: A comparative study with clinically used platinum derivatives." Cancer science 101.11 (2010): 2476-2482. (Year: 2010).*

Rudolf et al. Biometals (2010) 23:339-354 (Year: 2010).*

Europa. European Commission. Opinion on Zinc pyrithione, Scientific Committee on Consumer Safety, 2014, obtained from <URL: https://ec.europa.eu/health/scientific_committees/consumer_safety/docs/sccs_o_133.pdf> on Sep. 19, 2022. (Year: 2014).*

IMAP Report. Zinc, bis(1-hydroxy-2(1H)-pyridinethionato-O,S)-, (T-4)-: Human health tier II assessment. <https://www.industrialchemicals.gov.au/sites/default/files/Zinc%2C%20bis%281-hydroxy-2%281H%29-pyridinethionato-0%2CS%29-%2C%20%28T-4%29-_Human%20health%20tier%20II%20assessment.pdf> (Year: 2015).*

Andrabi, S., et al., "Poly(ADP-ribose) polymerase-dependent energy depletion occurs through inhibition of glycolysis", PNAS, vol. 111, No. 28: 10209-10214 (2014).

Andrews, L., et al., "LAG3 (CD223) as a Cancer Immunotherapy Target", Immunol Rev., 276(1): 80-96 (2017).

Aoki, T., et al., "Pitavastatin suppresses formation and progression of cerebral aneurysms through inhibition of the nuclear factor $_K$B pathway", Neurosurgery vol. 64, No. 2: 357-366 (2009).

Bajaj, I., et al, "Poly (glutamic acid) An emerging biopolymer of commercial interest", Bioresource Technology, vol. 102, No. 10: 5551-5561 (2011).

Burugu, S., et al., "Emerging Targets in Cancer Immunotherapy", Seminars in Cancer Biology, 52: 39-52 (2018).

Carraway, R., et al., "Zinc pyrithione induces ERK- and PKC-dependent necrosis distinct from TPEN-induced apoptosis in prostate cancer cells", Biochimica et Biophysica Acta, vol. 1823(2): 544-557 (2011).

Chae, Y., et al., "Current landscape and future of dual anti-CTLA4 and PD-1/PD-L1 blockade immunotherapy in cancer; lessons learned from clinical trials with melanoma and nonsmall cell lung cancer (NSCLC)", Journal for ImmunoTherapy of Cancer, 6;39 28 pages (2018).

Cho, Y., et al, "Harnessing of Programmed Necrosis for Fighting against Cancers", Biomolecules & Therapeutics 22(3): 167-175, (2014).

Cvek, B., et al, "Targeting of Nuclear Factor-$_k$B and Proteasome by Dithiocarbamate Complexes with Metals", Current Pharmaceutical Design 13: 3155-3167 (2007).

Freshney, R. Ian, "Culture of Tumor Cells" (Chapter 24) in: Culture of Animal Cells: A Manual of Basic Technique and Specialized Applications, Sixth Edition, Copyright 2010 John Wiley & Sons, Inc.: pp. 463-479 (2010).

Huang, Y., et al., "Targeting CD47: the achievements and concerns of current studies on cancer immunotherapy", J. Thorac. Disease, 9(2), E168-E174 (2017).

Iguchi, K., et al., "Induction of necrosis by zinc in prostate carcinoma cells and identification of proteins increased in association with this induction," European Journal of Biochemistry, vol. 253(3): 766-770 (1998).

Internet Article, "Recommended daily intake of vitamins and minerals", obtained from website: https:\\www.lenntech.com/recommended-daily-intake.htm (dated Jul. 6, 2005) (Year: 2005).

Kim, U., et al., "The Role of NADPH Oxidase and Neuronal Nitric Oxide Synthase in Zinc-Induced Poly(ADP-ribose) Polymerase Activation and Cell Death in Cortical Culture", Experimental Neurology 177: 407-418 (2002).

Knee, D., et al., "Rationale for anti-GITR cancer immunotherapy", European Journal of Cancer, 67:1-10 (2016).

Leamon, C., et al., "Synthesis and biological evaluation of EC20: a new folate-derived, $^{99m}$Tc-based radiopharmaceutical", Bioconjugate Chemistry 13: 1200-1210 (2002).

Mann, J., et al, "Zinc pyrithione induces apoptosis and increases expression of Bim", Apoptosis: vol. 10, No. 2: 369-379 (2005).

Maret, W., et al., "Zinc requirements and the risks and benefits of zinc supplementation," J. Trace Elem. Med. Biol. 20 (1 ): 3-18 (2006).

Mason, R. Preston, "Optimal therapeutic strategy for treating patients with hypertension and atherosclerosis: focus on olmesartan medoxomil", Vascular Health and Risk Management vol. 7: 405-416 (2011).

Nakano, A., et al, "Telmisartan inhibits cytokine-induced nuclear factor-kappaB activation independently of the peroxisome proliferator-activated receptor-gamma", Hypertension Research Official Journal of the Japanese Society of Hypertension 32: 765-769 (2009).

Peng, M., et al., "Degradation rate of rate of γ-polyglutamic acid probed by $^1$H-NMR spectral analysis and by PFGSTE NMR—internal consistency", IJRRAS 3 (3): 233-241 (Jun. 2010).

Perkins, D. J., "Zn2+ binding to poly-L-glutamic acid and human serum albumin," Biochimica et Biophysica Acta (BBA), vol. 86(3): 635-636 (1964).

Snyder, D., et al, "Neurological, microscopic and enzyme-histochemical assessment of zinc pyrithione toxicity", Food and Cosmetics Toxicology 17: 651-660 (1979).

Uchiyama, R., et al, "Involvement of Caspase-9 in the Inhibition of Necrosis of Raw 264 Cells Infected with Mycobacterium tuberculosis", Infection and Immunity vol. 75, No. 6: 2894-2902 (2007).

Vaitilingam, B., et al., "A Folate Receptor-α-Specific Ligand That Targets Cancer Tissue and Not Sites of Inflammation", The Journal of Nuclear Medicine 53: 1127-1134 (2012).

Willis, M., et al, "Zinc-induced Copper Deficiency: A Report of Three Cases Initially Recognized on Bone Marrow Examination," Am. J. Clin. Pathol. 123: 125-31 (2005).

Helsel, M.E., et al. "Pharmacological activity of metal binding agents that alter copper bioavailability", Dalton Transactions, vol. 44, No. 19, Mar. 23, 2015 (Mar. 23, 2015), pp. 8760-8770.

Kiew et al., "Near-infrared activatable phthalocyanine-poly-L-glutamic acid conjugate: increased cellular uptake and light-dark toxicity ratio toward an effective photodynamic cancer therapy," Nanomedicine: Nanotechnology, Biology, and Medicine, vol. 13: 1447-1458 (2017).

(56) References Cited

OTHER PUBLICATIONS

Li et al., "Poly(L-glutamic acid)-anticancer drug conjugates," Advanced Drug Delivery Reviews, vol. 54:695-713 (2002).
Sullivan, Gregory F., "Regulation of expression of the multidrug resistance protein MRP1 by p53 in human prostate cancer cells," The Journal of Clinical Investigation, vol. 105(9): 1261-1267 (2000).
Iitaka et al., "Induction of apoptosis and necrosis by zinc in human thyroid cancer cell lines," Journal of Endocrinology, vol. 169: 417-424 (2001).
Ku et al., The role of survivin and Bcl-2 in zinc-induced apoptosis in prostate cancer cells, Urologic Oncology: Seminars and Original Investigations, vol. 30: 562-568 (2012).

* cited by examiner

ZINC-[GAMMA]-PGA COMPOSITIONS AND METHODS FOR TREATING CANCER

CROSS-REFERENCE TO RELATED APPLICATIONS

This application is a United States National Stage filing under 35 U.S.C. § 371 of International Application No. PCT/SG2017/050545, filed on Oct. 31, 2017, which claims the benefit of and priority to Singapore Patent Application No. 10201609131Y, filed on Nov. 1, 2016, the contents of all of which are incorporated by reference herein in their entirety. International Application No. PCT/SG2017/050545 was published under PCT Article 21(2) in English.

FIELD OF THE INVENTION

The invention relates to compositions comprising gamma-polyglutamic acid (γ-PGA) carrier and a zinc salt, and, optionally, an NF-kB inhibitor, pharmaceutical formulations thereof, and methods using any of the compositions and formulations as anti-tumor agents to treat cancer in a patient.

BACKGROUND OF THE INVENTION

Inherent and acquired drug resistance to cancer drugs is a major cause of cancer treatment failures. Common mechanisms for resistance include dysfunctions in p53 apoptosis protein and/or overexpression of energy-dependent drug ejection pumps encoded by MDR1 or MRP1 genes. One tumoricidal strategy for overcoming the drug resistance problem is to individually correct the dysfunctional p53 apoptosis function or to inhibit the drug ejection pumps. An alternate approach is to utilize PARP1-mediated energy depletion-induced necrotic cell death mechanism ("PARP1-mediated necrosis") that bypasses the p53-mediated apoptosis mechanism altogether.

PARP1-mediated necrosis, initially observed in post-ischemic necrosis of heart or brain tissues, is caused by depletion of cellular energy (NAD$^+$ and ATP) from excessive DNA-repair activity by PARP1 enzyme. Hyperactivation of PARP1/PARG in response to genetic damage triggers depletion of NAD and ATP cellular energy commodities, which subsequently triggers mitochondria-initiated necrosis from MPTP activation. This set of events is illustrated in FIG. 1. Because the necrosis mechanism bypasses p53-mediated apoptosis, it was proposed that this mechanism could be used to target cancer (NPL3). However, no one succeeded in translating this idea into a clinically useful therapeutic treatment because the methods tried proved to be too toxic. PARP1-mediated necrosis could only be induced in experimental tumors by excessive radiation exposure and/or administration of highly toxic chemotherapeutic agents such as doxorubicin. Another problem with using toxic agents for activating PARP1-mediated necrosis was that the agents also activated p53 proteins at sub-critical levels, effectively disabling PARP1-mediated necrosis via p53-induced fragmentation of PARP1 enzymes. Given that drug distribution within a tumor is heterogeneous due to physical and structural constraints, it was inferred that toxic agents would simultaneously render a large portion of the cancer tumor mass devoid of PARP1 and therefore insensitive to PARP1-mediated necrosis.

The problem to be solved in a great number of clinical cancer cases is that some cancers are innately resistant to conventional anticancer drugs and others develop multidrug resistance over the course of systemic treatment, resulting in treatment failure. Although there was a theoretical suggestion that harnessing PARP1-mediated tumor necrosis through excessive dosing with radiation and chemotherapeutic agents could be used to treat cancer, realizing this potential result was difficult due to the inherent toxicity of the treatment and the inherent self-contradictory nature of the mechanism mentioned above. Thus, there remains an unmet need to find a composition and/or treatment method based on actively inducing PARP1-mediated tumor necrosis. Furthermore, a composition and/or treatment method comprising a carrier and targeting system that can specifically deliver such an inducer to tumor tissues without interfering with the tumor necrosis process or being excessively toxic is highly desired. There is also a continued desire to reduce the tumoricidal dose needed against a wide variety of cancer types and/or drug resistance traits, and to reduce unwanted side effects in healthy tissue.

A report assessing neurotoxicity of zinc salts describes that high concentrations of zinc ion from simple zinc salts (400 μM or 26 μg/mL) induces PARP/PARG-mediated NAD$^+$ and ATP depletion and subsequent necrosis in cultured cortical cells (NPL6). The report, however, did not study tumoricidal activity of zinc salts or their therapeutic use against cancer.

A report assessing the toxicity of zinc pyrithione against immune cells showed that nanomolar concentrations of zinc pyrithione induced zinc-specific apoptosis in various leukocyte-originating cells, including murine thymocytes, murine splenic lymphocytes, human Ramos B, and human Jurkat T cells (NPL7). The report disclosed that zinc pyrithione induced apoptosis via activation of caspase 9, which has the effect of blocking necrotic cell death (NPL11). Collectively, these reports indicate that nanomolar doses of zinc pyrithione induce apoptotic cell death and not necrotic cell death in the immune cells studied.

Later, it was demonstrated that micromolar concentrations of zinc pyrithione (1-10 μM) elicited ATP-depletion and, eventually, ERK and PKC-dependent necrosis in androgen-dependent LNCaP and androgen-independent PC3, DU145 prostate cancer cell lines (NPL2). However, the dose of zinc pyrithione used in NPL2 to elicit necrosis was previously shown to cause acute neurological toxicity in rats after 9~14 days of dietary administration (240 ppm) with clinical symptoms of progressive hind-limb weakness, motor incoordination, spinal kyphosis with muscle atrophy and penile prolapse (NPL10).

Thus, although there was a report that zinc pyrithione was capable of causing selective necrotic cell death against prostate cancer cell lines, it required high (μM) concentrations of the agent (NPL2), but zinc pyrithione had been shown to cause severe and permanent neurotoxicity at such concentrations (NPL12), which would have dissuaded attempting to develop it into an antitumor therapeutic agent. Furthermore, NPL2 did not demonstrate broad-spectrum anticancer activity against multiple cancer cell types, show efficacy towards reversing drug resistance arising from MDR1 or MRP1 multidrug resistance gene overexpression, or demonstrate necrotic efficacy in any animal cancer models.

NPL5 developed insulin-mimetic zinc (2+) complexes and investigated the in vitro insulin-mimetic activity as well as the in vivo antidiabetic effects in type-2 diabetic KKA$^y$ mice of zinc(gamma-polyglutamic acid) complexes. Specifically, the study showed that oral administration of 10-20 mg Zn per kg body mass for 30 days with gamma-polyglutamic acid-complexed zinc normalized the hyperglycemia in KKA$^y$ mice, and improved the impaired glucose tolerance, elevated HbA(1c) levels, and metabolic syndromes relative to treatment with ZnSO$_4$ (NPL5). In NPL5, the authors concluded that the zinc(gamma-polyglutamic acid) complexes have antidiabetic potency through their high blood glucose-lowering effect and their ability to attenuate the derangement in β cell secretion of insulin and the insulin resistance in type-2 diabetic KKA$^y$ mice, however they did not understand the mechanism of action responsible for the insulin-mimetic activity of the complex, and they did not suggest in any way antitumor activity by zinc(gamma-polyglutamic acid) complexes nor its effectiveness for treating drug-refractory cancer types.

In summary, the art has not even suggested, much less succeeded in using zinc compounds to achieve the above-mentioned goal of effectively treating broad-spectrum cancers in vivo, including those with important drug-resistance traits, and moreover to do so without risking severe toxicity. Hence, there is an unmet need for a clinically active and safe zinc composition for treating cancer that works across many cancer types and even those having drug-resistance phenotypes (e.g., dysfunctional p53, MDR1 overexpression, MRP1 overexpression), without toxicity issues. To solve the problem we performed systematic research in the field and developed formulations of zinc complexes meeting these needs, and accordingly completed our invention as described herein.

CITATIONS

NPL1. Aoki, T., Kataoka, H., Ishibashi, R., Nakagami, H., Nozaki, K., Morishita, R., and Hashimoto, N. (2009). Pitavastatin suppresses formation and progression of cerebral aneurysms through inhibition of the nuclear factor kappaB pathway. *Neurosurgery* 64, 357-365; discussion 365-356.

NPL2. Carraway, R. E., and Dobner, P. R. (2012). Zinc pyrithione induces ERK- and PKC-dependent necrosis distinct from TPEN-induced apoptosis in prostate cancer cells. *Biochimica et Biophysica Acta* 1823, 544-557.

NPL3. Cho, Y. S., and Park, S. Y. (2014). Harnessing of Programmed Necrosis for Fighting against Cancers. *Biomolecules & Therapeutics* 22, 167-175.

NPL4. Cvek, B., and Dvorak, Z. (2007). Targeting of nuclear factor-kappaB and proteasome by dithiocarbamate complexes with metals. *Current Pharmaceutical Design* 13, 3155-3167.

NPL5. Karmaker, S., Saha, T. K., Yoshikawa, Y., and Sakurai, H. (2009). A Zinc(II)/poly(gamma-glutamic acid) complex as an oral therapeutic for the treatment of type-2 diabetic KKAy mice. *Macromolecular Bioscience* 9, 279-286.

NPL6. Kim, Y. H., and Koh, J. Y. (2002). The role of NADPH oxidase and neuronal nitric oxide synthase in zinc-induced poly(ADP-ribose) polymerase activation and cell death in cortical culture. *Experimental Neurology* 177, 407-418.

NPL7. Mann, J. J., and Fraker, P. J. (2005). Zinc pyrithione induces apoptosis and increases expression of Bim. *Apoptosis: An International Journal on Programmed Cell Death* 10, 369-379.

NPL8. Mason, R. P. (2011). Optimal therapeutic strategy for treating patients with hypertension and atherosclerosis: focus on olmesartan medoxomil. *Vascular Health and Risk Management* 7, 405-416.

NPL9. Nakano, A., Hattori, Y., Aoki, C., Jojima, T., and Kasai, K. (2009). Telmisartan inhibits cytokine-induced nuclear factor-kappaB activation independently of the peroxisome proliferator-activated receptor-gamma. *Hypertension Research: Official Journal of the Japanese Society of Hypertension* 32, 765-769.

NPL10. Snyder, D. R., de Jesus, C. P., Towfighi, J., Jacoby, R. O., and Wedig, J. H. (1979). Neurological, microscopic and enzyme-histochemical assessment of zinc pyrithione toxicity. *Food and Cosmetics Toxicology* 17, 651-660.

NPL11. Uchiyama, R., Kawamura, I., Fujimura, T., Kawanishi, M., Tsuchiya, K., Tominaga, T., Kaku, T., Fukasawa, Y., Sakai, S., Nomura, T., et al. (2007). Involvement of caspase-9 in the inhibition of necrosis of RAW 264 cells infected with *Mycobacterium tuberculosis*. *Infection and Immunity* 75, 2894-2902.

NPL12. Vaitilingam, B., Chelvam, V., Kularatne, S. A., Poh, S., Ayala-Lopez, W., and Low, P. S. (2012). A folate receptor-α-specific ligand that targets cancer tissue and not sites of inflammation. *The Journal of Nuclear Medicine* 53, 1127-1134.

NPL13. Leamon, C. P., Parker, M. A., Vlahov, I. R., Xu, L., Reddy, J. A., Vetzel, M., and Douglas, N. (2002). Synthesis and biological evaluation of EC20: a new folate-derived, $^{99m}$Tc-based radiopharmaceutical. *Bioconjugate Chemistry* 13, 1200-1210.

SUMMARY OF THE INVENTION

Compositions, pharmaceutical formulations, and methods disclosed herein are based on the surprising observation that complexes of zinc and γ-polyglutamic acid (γ-PGA) can induce necrotic cell death in various human and mouse cancer cell lines.

The present invention relates to a zinc-containing γ-polyglutamic acid composition that triggers a PARP1-mediated necrotic cell death mechanism. Without being limited by theory, zinc apparently over-activates PARP1, which in turn leads to depletion of ATP and NAD+ in cells. As a result, the cells are depleted of energy sources, and then enter a necrotic cell death pathway.

This mechanism to induce necrosis is expected to be similarly available for most cancer cell types and thus zinc-containing γ-polyglutamic acid compositions demonstrate broad-spectrum tumoricidal activity. Furthermore, this mechanism suggests that tumors having a drug-resistant phenotype with respect to different tumoricidal mechanisms may also respond to this PARP1-mediated mechanism.

Compositions according to the invention comprise (i) zinc(II) species (equivalently, Zn$^{2+}$) as an active ingredient and (ii) γ-PGA as a carrier in a unmodified form and/or modified form, wherein folic acid and/or RGD tumor targeting peptides are covalently joined to γ-PGA. Compositions may further comprise NF-kB inhibitors or NF-kB signaling cascade inhibitors to sensitize the tumor cells (make them more susceptible to) the tumoricidal effect of Zn(II) and γ-PGA.

The compositions may be formulated for oral administration. In some embodiments, oral formulations that comprise gastro-resistant materials, such as enteric bindings and coatings, or wax coatings, to prevent, delay, or attenuate dissociation of zinc ions from the complex in the strongly acidic environment of the stomach are provided.

The invention also relates to methods for preparing the above-mentioned compositions and pharmaceutical formulations, and the therapeutic uses thereof.

It is one object of the invention to provide a composition that can actively induce PARP1-mediated tumor necrosis, and it is a further object to do so using compositions and formulations that are not toxic to the patient.

It is another object of the invention to provide pharmaceutical formulations for use in treating a wide variety of tumors and cancer cells having drug-resistant phenotypes in a patient.

It is another object of the invention to provide a composition comprising a γ-PGA carrier that can target delivery of Zn(II) to tumor cells. Also, it is an object of the invention to provide a strong tumoricidal agent having a reduced dose requirement, or with reduced profile of unwanted side effects in healthy tissue.

One embodiment of a method of inducing PARP1-mediated tumor necrosis in a tumor in a patient comprises administering a therapeutically effective amount of a Zn(II) salt and a γ-polyglutamic acid carrier to the patient with the tumor wherein said γ-polyglutamic acid carrier comprises γ-polyglutamic acid and/or a tumor-targeting γ-polyglutamic acid derivative and/or a charge-modified γ-polyglutamic acid derivative and/or a tumor-targeting charge-modified γ-polyglutamic acid derivative. In another embodiment of a method, a therapeutically effective amount of a Zn(II) salt and a γ-polyglutamic acid carrier (unless otherwise indicated, reference to a γ-polyglutamic acid carrier or composition includes compositions comprising the various types of derivatives of γ-polyglutamic acid as listed above) are administered to a patient with a tumor that has a drug-resistant phenotype.

In another embodiment of a method, a therapeutically effective amount of a Zn(II) salt and a γ-polyglutamic acid carrier are administered in combination with a therapeutic amount of an NF-κB inhibitor and/or an NF-κB signaling cascade inhibitor.

In one embodiment, a therapeutic amount of Zn(II) salt and γ-polyglutamic acid carrier are administered together in a solid dosage form or in a liquid dosage form. In several embodiments, a solid dosage form is selected from a tablet, a minitab, a hard capsule, a soft capsule, a caplet, a gelcap, an oral disintegrating films, granules, pellets, a paste, and a powder sachet. In several embodiments, a liquid dosage form is selected from a liquid solution, a liquid suspension, a syrup, and an oral spray.

In several embodiments, a therapeutic amount of Zn(II) salt and γ-polyglutamic acid carrier is administered together by oral administration or an injection administration.

One embodiment of the invention is a pharmaceutical composition comprising (i) a pharmaceutically acceptable Zn(II) salt, (ii) γ-polyglutamic acid containing a tumor-targeting moiety and/or a charge-modifying moiety, and (iii) optionally further comprising γ-polyglutamic acid.

In several embodiments said tumor-targeting moiety is selected from folic acid, dimethyl tetrahydrofolate (DMTHF), and RGD peptide, and any combination of said moieties are covalently joined to γ-polyglutamic acid. In several embodiments said charge-modifying moiety is selected from citric acid, ethylenediamine tetraacetic acid, 1,4,7,10-tetracyclododecane-N,N',N'',N'''-tetraacetic acid, and diethylenetriamine pentaacetic acid, and any combination of said moieties are covalently joined to γ-polyglutamic acid.

In another embodiment, the pharmaceutical compositions further comprise γ-polyglutamic acid. In another embodiment, in the pharmaceutical compositions a substantial portion of said Zn(II) salt is a bound complex of the Zn(II) ion with γ-polyglutamic acid and/or said tumor-targeting moiety and/or said charge-modifying moiety. In another embodiment, in the pharmaceutical compositions a Zn(II) salt and (ii) said γ-polyglutamic acid polymers are mixed together in a solid mixture.

In another embodiment, the pharmaceutical compositions further comprise an NF-κB inhibitor and/or an NF-κB signaling cascade inhibitor.

In other embodiments, any of the above pharmaceutical compositions are formulated as a solid dosage form. In several further embodiments, the solid dosage forms further comprise a gastro-resistant binder and/or a gastro-resistant outer coating. In other embodiments, any of the above pharmaceutical compositions are formulated as a liquid dosage form. In some embodiments, the liquid dosage form is formulated for injection. In further embodiments, the liquid dosage form is a suspension of a pharmaceutical composition that further comprises a gastro-resistant material. In further embodiments, the liquid dosage form is a suspension of a wax-coated microparticles comprising any of the above pharmaceutical compositions and, optionally, a gastro-resistant material.

One embodiment of a method for treating a tumor in a patient comprises administering a therapeutically effective amount of a pharmaceutical composition according to any one of the foregoing embodiments of a pharmaceutical composition to the patient with the tumor. In a further embodiment of the method, a therapeutically effective amount of the foregoing pharmaceutical compositions are administered to a patient with a tumor that has a drug-resistant phenotype.

These and other objects and features of the invention will become apparent to one of ordinary skill in the art from the following detailed description of the invention and the claims.

DETAILED DESCRIPTION OF THE INVENTION

Figure 1:
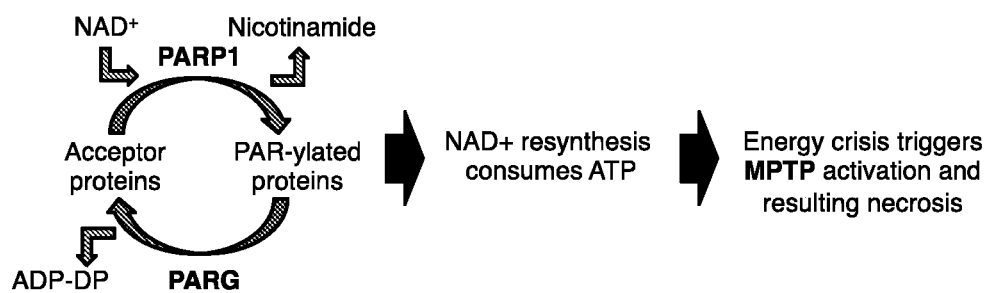
FIG. 1 is a schematic summary of PARP1-mediated necrosis.

The components used in the compositions, formulations, and methods described herein are of a grade accepted by regulatory authorities for pharmaceutical use, or for use in foods, or for use in products for human consumption. In some instances the components are pharmaceutical grade or medical grade compounds or substances.

The meaning of abbreviations used herein is as follows: "kDa" means kiloDalton; "wt %" means percent by weight.

Zinc is provided as a zinc(II) salt (equivalently, a $Zn^{2+}$ salt), wherein the counterion (anion) may be any suitable inorganic or organic anion. Suitable anions are those that are tolerated by the human body, including those that are not toxic. Generally, the zinc salt can be represented by the formulas $Zn^{2+}X^{2-}$ or $Zn^{2+}(X^-)_2$ or even $Zn^{2+}(X^-)(Y^-)$, where X and Y are suitable anions. The anion may be selected from the group of anions that are a component of an approved pharmaceutical. In some embodiments, the zinc (II) salt is a pharmaceutically acceptable zinc salt, wherein said zinc(II) salt is selected from the group of zinc(II) salts that have been approved for use in pharmaceutical compositions. The anion may be selected from the group of anions that are a component of an FDA-approved pharmaceutical product. In some embodiments, the zinc(II) salt is a pharmaceutically acceptable zinc salt. In other embodiments, the anion may be selected from the group anions that are a component of an approved food additive or nutritional supplement. Examples of zinc salts include zinc chloride, zinc sulfate, zinc citrate, zinc acetate, zinc picolinate, zinc gluconate, amino acid-zinc chelates, such as zinc glycinate, or other amino acids known and used in the art. Two or more different zinc salts may be used together in any proportion for providing Zn(II) in any of the compositions or formulations.

In some embodiments, Zn(II) is provided complexed to γ-polyglutamic acid compounds in the composition or formulation. Typically, when complexed forms of Zn(II) and γ-PGA ("ZnPGA") are provided, the ZnPGA is purified and free Zn(II) ions as well as the original counterions to the Zn cation are substantially removed in the process.

The amount of zinc included in a single solid dosage form is generally in the range of about 1 to about 100 mg of zinc (zinc(II) ion). Thus, the particular amount of zinc salt(s) used in a formulated composition will be higher because amount of the salt must account for the weight of the counterion. Considering only zinc(II), the amount provided in a dosage form may be up to about 100 mg, up to about 75 mg, up to about 50 mg, up to about 25 mg, up to about 10 mg of zinc, or up to about 5 mg. The amount of zinc(II) provided in a solid dosage form is generally at least about 1 mg. By way of comparison, commonly available supplements provide, for example, 20, 25, 30, 50, 75, and even 100 mg of zinc. Any amount of zinc in this range, or even higher, is acceptable so long as the amount provided does not cause physiologically excessive levels of zinc to be absorbed. What might be considered an excessive level and the risk therefrom, however, is to be balanced against the therapeutic benefit gained by treating a tumor. Although a tolerable upper intake level of zinc in most adults is about 40 mg/day (and for children it is lower), it should be recognized that all of the zinc in the solid dosage form taken orally is unlikely to be absorbed; some of it will pass through the body without being adsorbed. Because the amount of zinc absorbed will also vary with the formulation, the upper limit for zinc content in a particular formulation can be tested by methods known in the art to ascertain the level of uptake provided by the formulation, and then in view of any therapeutic benefit in the treatment gained by administering the formulation, one may adjust the amount administered for a given dosage form or formulation accordingly.

The concentration of zinc provided in a composition or formulation in a liquid dosage form is generally in the range of about 1 mg/L to about 100 g/L of zinc (zinc(II) ion). This corresponds to a range of about 0.0001 wt % to about 10 wt % of zinc. The concentration of Zn(II) may be at least about 10 mg/L, or at least about 100 mg/L, or at least about 1 g/L, or at least about 10 g/L, or the range for the concentration of Zn(II) may fall within any two of these exemplary concentrations. In one embodiment, the concentration may be in the range of about 100 mg/L about 500 mg/L. The amount of the liquid provided in the dosage form will determine the total dosage amount. For example, 100 mL amount of liquid would provide about 10 mg to about 50 mg of Zn(II) for the exemplary range. In another embodiment, the concentration may be about 1000 mg/L (1 mg/mL), and thus provide about 1 mg per milliliter. The disclosure regarding dosage amounts of zinc in solid dosage forms may be used as guidance as to the amount of Zn(II) solutions to provide as a liquid dosage amount. As disclosed in Example 4, mice were treated with 160 μg/mL solutions of Zn(II) (equal to 160 mg/L) and received a physiologically relevant dose of 16 mg/day/kg body weight of Zn(II).

Zinc may also be provided as part of a solid suspended in liquid. The amount of zinc(II) and the volume of the suspension provided follows the guidance set out above for solid and liquid dosage forms.

Gamma-polyglutamic acid (alternatively γ-polyglutamic acid or γ-PGA) is a polymer of glutamic acid, an amino acid, where the polymer backbone is formed by a peptide bond joining the amino group and carboxyl group in the amino acid side chain (at the γ-carbon). γ-PGA can be formed from the L isomer, the D isomer, or the DL racemate of glutamic acid. Any of these forms may be used, and two or more different forms may be used together in any proportion. The various isomeric forms of γ-PGA may be synthetic or derived from natural sources. γ-PGA is found, for example, in Japanese natto and in sea kelp. Whereas organisms usually only produce poly(amino acids) from the L isomer, certain bacterial enzymes that produce γ-PGA can produce polymers from either isomer or both isomers.

γ-PGA of various sizes and various polymer dispersities may be used. The polymer molecular weight of γ-PGA is generally at least about 1 kDa and at most about 1000 kDa. In some embodiments, the polymer molecular weight of γ-PGA is at least about 1 kDa, or at least about 5 kDa, or least about 10 kDa, or at least about 20 kDa, or least about 30 kDa, or at least about 35 kDa, or at least about 40 kDa, or at least about 50 kDa. In some embodiments, the polymer molecular weight of γ-PGA is at most about 700 kDa, or at most about 500 kDa, or at most about 300 kDa, or at most about 200 kDa, or at most about 100 kDa. An acceptable polymer molecular weight range may be selected from any of the above indicated polymer molecular weight values. In an embodiment, the polymer molecular weight is in the range of about 5 kDa to about 500 kDa. In another embodiment, the polymer molecular weight is in the range of about 5 kDa to about 300 kDa. In an embodiment, the polymer molecular weight is in the range of about 50 kDa to about 100 kDa. In one embodiment, the polymer molecular weight is about 100 kDa. In one embodiment, the polymer molecular weight is about 50 kDA. A composition or formulation may comprise one or more polymer molecular weight forms of γ-PGA.

Polymer molecular weights are typically given as a number average molecular weight ($M_n$) based, for example, on a measurement by gel permeation chromatography (GPC). The above polymer masses are cited as $M_n$; other measurement techniques can be used to determine, e.g., a mass (weight) average molecular weight ($M_w$), and the specification for any given polymer can be converted among the various polymer mass representations.

The amount of γ-PGA included in a solid dosage form is generally in the range of about 10 wt % to about 40 wt %. In some embodiments the amount is about 20 wt % or about 30 wt %. The amount used is generally based upon the desired molar ratio between zinc and polyglutamic acid monomer units, the mass of the zinc salt (accounting for the weight of the counterion), and the amount of excipients needed to provide an acceptable formulated dosage form. For example, the greater the amount of γ-PGA and zinc salt used, the lesser the amount of excipients that can be added for a given overall dosage form size. Those of skill in the art can readily balance the amount of active ingredients versus the amount and type of excipients needed to obtain stable dosage forms. The desired ratio between zinc and γ-PGA can also be expressed as a ratio of milligrams of zinc to wt % of γ-PGA per dosage form. Exemplary ratios include 5 mg: 10 wt %; 5 mg: 20 wt %; 5 mg: 40 wt %; 30 mg: 10 wt %; 30 mg: 20 wt %; 30 mg: 40 wt %; or even 100 mg: 10 wt %; 100 mg: 20 wt %; 100 mg: 40 wt %; or any other sets of values within the ranges set forth by these exemplary ratios or that are apparent from the values cited for each ingredient in this specification.

The amount of γ-PGA included in a liquid dosage form is generally in the range of about 0.01 wt % to about 10 wt %. In some embodiments the amount is about 0.1 wt % to about 1 wt %.

The amount used is generally based upon the desired molar ratio between zinc and polyglutamic acid monomer units, the nature of the γ-PGA carrier (that is whether it is unmodified, or modified with a tumor-targeting moieties and/or a charge-modifying moieties), and the degree of formation of Zn(II) complexes with the γ-PGA carrier. For example, as illustrated in Examples 1 and 2, ZnPGA complexes were obtained as solution comprising approximately 1 wt % γ-PGA with approximately 400 µg/mL (mg/L) of complexed zinc. Without being bound by theory, it should be understand that when preparing liquid dosage forms, combining a zinc salt with a γ-PGA carrier in solution will generally result in formation of complexes of the zinc ion and γ-PGA carrier, so a separate step of isolating or purifying the formed complex may not be necessary. Other exemplary ratios include the ranges based upon the disclosures above regarding the concentration of zinc provided in a composition or formulation in a liquid dosage form in combination with the amount of γ-PGA included in a liquid dosage form.

To arrive at suitable solid or liquid compositions and formulations having an effective amount of a Zn(II) salt and a γ-polyglutamic acid carrier, the relative amounts and the respective concentrations of γ-PGA carrier and zinc can be adjusted readily by those of skill in the art in accordance with the disclosure. In the compositions disclosed herein, the γ-PGA component may be referred to as γ-PGA or as γ-PGA carrier. As noted, derivatives of γ-PGA are also contemplated, and may be variously referred to as modified γ-PGA or γ-PGA conjugate, and the like.

γ-PGA may comprise tumor-targeting moieties. Such moieties may be selected from folic acid, $N^5,N^{10}$-dimethyl tetrahydrofolate (DMTHF), and RGD peptide. Any or all of said moieties may be covalently joined to γ-polyglutamic acid to form a folate conjugate and/or a DMTHF conjugate and/or an RGD peptide conjugate of γ-PGA. Folate receptor protein is often expressed in many human tumors.

Folates naturally have a high affinity for the folate receptors, and further, upon binding, the folate and the attached conjugate may be transported into the cell by endocytosis. In this way, a ZnPGA modified with folic acid can target and accumulate at tumor cells and deliver zinc(II) to the inside of the tumor cells. DMTHF is also known to have a high affinity for folate receptors. The preparation of DMTHF is described in NPL13. Furthermore, there are two major isoforms of the folate receptor (FR), FR-α and FR-β, and DMTHF has been shown to have a higher affinity for FR-α over FR-β (NPL12). This is beneficial for targeting tumor cells because FR-α is overexpressed in many malignant cell types, whereas FR-β is overexpressed on macrophages associated with inflammatory disease, Thus, conjugating DMTHF to γ-PGA provides a conjugate that may selectively bind to folate receptors expressed by tumor cells. Similarly, RGD peptides are known to bind strongly to α(V)β(3) integrins, which are expressed on tumoral endothelial cells as well as on some tumor cells. Thus RGD conjugates are a strategy for targeting and delivering antitumor agents to the site. As contemplated in this invention, γ-PGA may be conjugated (i.e., modified) with any one or two, or all of these tumor targeting agents, and when two or more are present, the relative ratio of these agents is not particularly limited. For example, a γ-PGA carrier may comprise a conjugate of γ-PGA with (a) folic acid, (b) DMTHF, (c) RGD, (d) folic acid and DMTHF, (e) folic acid and RGD, (f) DMTHF and RGD, or (g) folic acid, DMTHF, and RGD. Other similar tumor targeting moieties are also within the scope of the invention.

γ-PGA has a free carboxylic acid group at the α-carbon of each glutamic acid unit that can be used to form a conjugate with folic acid, with DMTHF, and with RGD peptide. Folic acid has an exocyclic amine group that may be coupled with the α-carbon carboxylic acid group of glutamic acid to form an amide bond joining the two. The same exocyclic amine group as in folic acid is available in DMTHF for amide bond formation. RGD conjugates are also well-known in the art, and can also be similarly covalently joined to the α-carbon carboxylic acid group via, for example, the free α-amino group in RGD. Alternatively, either moiety may be conjugated to γ-PGA via a spacer group, such as, for example, polyethylene glycol amine. Examples of conjugation reactions to γ-PGA, including that of folic acid and citric acid, can be found in WO 2014/155142 (published Oct. 2, 2014).

γ-PGA may comprise charge-modifying moieties. Such moieties may be selected from citric acid, ethylenediamine tetraacetic acid (EDTA), 1,4,7,10-tetracyclododecane-N, N',N",N"'-tetraacetic acid (DOTA), and diethylenetriamine pentaacetic acid (DTPA). Any combination of said moieties may be covalently joined to γ-polyglutamic acid, again, at the α-carbon carboxylic acid. Citric acid may be conjugated to the α-carbon carboxylic acid group of γ-PGA by forming an ester linkage. (See, e.g., WO 2014/155142.) EDTA, DOTA, and DTPA may be joined to γ-PGA using, for example, spacer groups to join the amines of these moieties to the α-carbon carboxylic acid group of γ-PGA. Numerous options are available to one of skill in the art. The charge-modifying moieties can be used as sites for chelating Zn(II) ions, and the charge-modification will also affect transport and solubility of the ZnPGA complexes and as such can be used to tune the pharmaceutical effects of the carrier and the ZnPGA complexes.

γ-PGA may comprise both tumor-targeting and charge-modifying moieties so that the benefits and functionality of both types of moieties may be imparted to the γ-PGA carrier. Any combination of the tumor-targeting and charge-modifying moieties may be conjugated to γ-PGA, and the relative ratio of the moieties is not particularly limited.

Compositions and formulations according to the invention may also comprise an NF-κB inhibitor. As used herein, an NF-κB inhibitor includes direct inhibitors as well as compounds that can inhibit the signaling cascade, or any compound that suppresses the effect of NF-kB and thereby limits the proliferation or survival of tumor cells. Exemplary compounds that may be used as an NF-κB inhibitor as defined herein include pyrrolidine thiocarbamate (PDTC) (NPL4), telmisartan (NPL9), olmesartan (NPL1), valsartan (NPL8), disulfiram (NPL4), or pharmaceutically acceptable salts thereof. These inhibitors may also be referred to as sensitizers, because they limit the viability of tumor cells and thereby sensitize them to the effect of other tumoricidal agents, such as the compositions and formulations of the subject invention. Example 4 shows the tumoricidal effects of co-administration of PDTC and a formulation according to one embodiment of the invention.

Liquid Formulations

The zinc(II) and γ-PGA carrier ingredients can be formulated as a liquid. Suitable liquid formulations include a liquid solution, a liquid suspension, a syrup, and an oral spray. The liquid solutions can be taken orally or administered by injection, such intravenously, intradermally, intramuscularly, intrathecally, or subcutaneously, or directly into or in the vicinity of a tumor, whereas liquid suspensions, syrups and sprays are generally appropriate for oral administration.

Methods of Preparing Liquid Dosage Forms

Methods for preparing liquid dosage forms comprises mixing together the desired amounts of (i) zinc salt(s) and γ-PGA carrier and/or (ii) a ZnPGA complex, along with suitable excipients. Some embodiments further comprise a gastro-resistant binder and/or coating in the formulation.

A liquid solution formulation may be prepared with suitable carriers, diluents, buffers, preservatives, or other excipients suitably selected with regard to the form of administration. For example, intravenous formulations may be prepared buffered at a suitable pH and with isotonicity agents.

An embodiment of a liquid formulation suitable for injection or oral delivery comprises a zinc(II) salt, γ-PGA carrier (unmodified γ-PGA and/or any forms of modified γ-PGA, as described above), and water. In further embodiments, the liquid formulation may further comprise a buffer and/or a salt, such as sodium chloride. When a buffering agent is included, a preferred buffering pH is in the range of about pH 4 to about pH 9. When injected, preferably the solution is isotonic with the solution into which it is to be injected and of suitable pH. In one embodiment, zinc sulfate heptahydrate, γ-PGA, and sodium chloride are combined in water, wherein the concentration of zinc(II) is 1 mg/mL and γ-PGA is 10 mg/mL. The polymer molecular weight of γ-PGA may be selected from any of the ranges described above. In one embodiment, it is in the range of about 5 kDa to about 100 kDa, and in other embodiments it is in the range of about 1 kDa to about 100 kDa. In any embodiment, one or more polymer molecular weight forms of γ-PGA may be included.

In some embodiments, zinc salt(s) and a γ-PGA carrier may be prepared as a ZnPGA complex. Generally, to form a ZnPGA complex the zinc salt(s) and γ-PGA carrier are combined and purified as described, for example, in Examples 1 and 2. The solution of the obtained ZnPGA complex may be diluted or substantially dried and reconstituted in more concentrated form for use in the procedure for preparing a liquid dosage form. ZnPGA complexes may be formulated as injectable solutions, or as a liquid suspension, syrup, or spray.

Zinc salts and γ-PGA compositions can be formulated as a liquid suspension for use in methods of the invention. For example, first, granulated compositions comprising mixtures of a Zn(II) salt and a γ-PGA carrier (including unmodified and/or any modified forms of γ-PGA) are prepared with a gastro-resistant binder included in the granulated solid. (See discussion below regarding methods of preparing solid formulations.) The γ-PGA carrier may be prepared from γ-PGA having an average molecular weight in the range of about 5 kDa to about 500 kDa, or about 1 kDa to about 500 kDa, or about 5 kDa to about 100 kDa, or about 1 kDa to about 100 kDa. The granulated solid is then suspended in an acidic liquid suitable for ingestion. The pH of the solution may be less than about pH 6 so that the granulated solid remains stable as a result of the gastro-resistant binder. In one embodiment the liquid suspension formulation also contains a thickening agent or viscosity enhancer, such that the granulated solids can remain suspended sufficiently and be efficiently ingested from the container.

In another embodiment of a liquid suspension, the granulated solid is prepared by first preparing a ZnPGA complex, where Zn(II) is complexed with the γ-PGA carrier. Examples of such preparations are provided in Examples 1 and 2, for example. Thereafter the ZnPGA can be granulated with a gastro-resistant binder, and other suitable excipients. Then, this granulated mixture can be prepared as liquid suspension as described immediately above.

Another embodiment of a liquid formulation comprises forming particles, such as microspheres, microparticles, granules, or other suitable solid form of a zinc salt and γ-PGA complex, and coating the particle with a thin layer of wax. In preferred embodiments the particles further comprise a gastro-resistant binder. The coated particles are formulated as a liquid suspension formulation. The wax coating on the particles promotes physical integrity of the particle and reduces permeability, though the coating nonetheless permits delivery of the zinc and γ-PGA complex to the intestine.

Granules suitable for coating may be prepared according to any of the aforementioned methods. Microspheres or microparticles of a zinc salt, γ-PGA, and a gastro-resistant binder may be prepared by any of the numerous methods known in the art, which include the single emulsion method, double emulsion method, polymerization, interfacial polymerization, phase separation and coacervation, spray drying, spray congealing, solvent extraction, freeze drying of a dispersed phase. The dimensions of such microspheres or microparticles may range from tenths of a micron to thousands of microns. As an example, one method for preparing microspherical particles involves stirring a finely divided (e.g., powdered) solid mixture comprising a zinc salt and γ-PGA in a suspension medium such as paraffin oil, and adding a solution of a polymeric gastro-resistant binder to the stirred suspension. When the microspheres have formed a non-solvent, such as chloroform, is added to precipitate the microspheres, which are collected, dried, and subsequently coated with a wax.

Wax coatings are recognized to be biocompatible and non-immunogenic, and suitable for the entrapment and delivery of drugs to the intestinal tract. Particles (microspheres, microparticles, granules, and the like) may be coated with waxes, such as Carnauba wax, beeswax, cetostearyl alcohol, spermaceti, and other waxes, according to methods as known in the art. For example, particles may be coated with Carnauba wax by dissolving the wax in white paraffin oil, cooling the solution to less than 45° C., and then adding the particles to a mechanically-stirred wax/paraffin oil solution until the particles are coated. The stirring speed and time, and temperature of the wax solution can be adjusted to modify the thickness of the wax coating.

The wax-coated zinc salt and γ-PGA particles are formulated as a liquid suspension for administration. The coated zinc/γ-PGA particles are present at about 5 wt % to 30 wt % in the final formulated suspension. Typically, the liquid suspension formulation comprises a suspending polymer, a viscosity agent, and a buffer. The formulation may also further comprise one or more of a sweetener, a flavoring agent, and/or a preservative.

A suspending polymer may be selected from xanthan gum, carbomer, microcrystalline cellulose, carboxymethylcellulose, and sodium carboxymethylcellulose, which may be used singly or in any combination. Other similar agents as known in the art may also be used. In total, the suspending polymer component is present at about 0.02 wt % to about 5 wt % in the final formulation.

A viscosity agent may be selected from glycerin, hydroxypropyl cellulose, hydroxypropyl methylcellulose, povidone, guar gum, and locust bean gum, which may be used singly or in any combination. Other similar agents as known in the art may also be used. In total, the viscosity agent component is present at about 0.05 wt % to about 50 wt % in the final formulation.

A buffer may be selected from phosphate buffer, an acetate buffer, a lactate buffer, and a citrate buffer, or other pharmaceutically acceptable buffer that has a buffering capacity in the designated range. The buffering agents are adjusted to have pH of about 6 or lower. In some embodiments, the pH is between about 3 and about 6. In some embodiments, the pH is between 4.5 and 5, in other embodiments the pH is between 4 and 5, and in yet other embodiments the pH is between 3 and 5.

A sweetener may be selected from sucrose, invert sucrose, xylitol, sorbitol, maltitol, aspartame, saccharine, and sucralose, which may be used singly or in any combination. Other similar agents as known in the art may also be used. In total, the sweetener component may be present from about 5 wt % to 40 wt % in the final formulation.

A flavoring agent may be selected from any pharmaceutically acceptable flavoring agent, or any agent used in foods or supplements as known in the art, and may be added in amounts in the final formulation that are consistent with industry practice.

A preservative may be selected from sodium benzoate, methyl paraben, propyl paraben, benzyl alcohol, potassium sorbate, and citric acid, which may be used singly or in any combination, and may be added in amounts in the final formulation that are consistent with industry practice. Other similar agents as known in the art may also be used.

A formulation and a method for preparing a liquid dosage form according to some embodiments are provided below in Example 10.

In any of these embodiments for a liquid suspension formulation, the γ-PGA carrier generally is present in a concentration of about 0.01 wt % to about 10 wt %, and in some embodiments the amount is about 0.1 wt % or about 1 wt %. Zn(II) is generally present in a concentration of about 0.001 wt % to about 10 wt %.

Liquid dosage formulations may also be prepared to include NF-κB inhibitors. In embodiments that do not include such NF-κB inhibitors in the formulation, the NF-κB inhibitor may be co-administered using any other suitable formulation and form of administration.

Solid Formulations

The zinc salt and γ-PGA carrier can be formulated into oral solid dosage forms for oral administration such as a tablet, a hard capsule, a soft capsule or related forms such as a minitablet, a caplet, a gelcap, an oral disintegrating film, and the like. The dosage form is further formulated to include a gastro-resistant binder and/or gastro-resistant coating.

The zinc salt and γ-PGA carrier are combined with excipients suitable for use in a pharmaceutical product and suitable for making a particular dosage form, such as a tablet or a capsule, and the like. Typical excipients include fillers, binders, disintegrants, glidants, lubricants, as well as buffers, preservatives, anti-oxidants, flavoring agents, sweeteners, coloring agents, and the like. The amount and type of excipient to be added can be selected for various purposes, such as improved integrity of the dosage form, improved bioavailability, stability, manufacturing, coating, appearance, and/or compliance. Some excipients may serve more than one purpose and/or provide more than one improved characteristic.

Fillers may be water soluble or water insoluble, and one or more of each type may be combined. Examples of water soluble fillers include, without limitation, sugars such as glucose, fructose, sucrose, mannose, dextrose, galactose, and the like, and sugar alcohols, such as mannitol, sorbitol, xylitol, and the like, as known in the art. Examples of water insoluble fillers include, without limitation, waxes, long-chain fatty acids, talc, kaolin, silicon dioxide, titanium dioxide, alumina, starch, powdered cellulose, microcrystalline cellulose, and the like, as known in the art.

Binders include, without limitation, cellulose derivatives such as carboxymethylcellulose calcium, carboxymethylcellulose sodium, cellulose acetate phthalate, ethyl cellulose, hydroxyethyl cellulose, hydroxyethylmethyl cellulose, hydroxypropyl cellulose, hydroxypropyl methyl cellulose, methyl cellulose, microcrystalline cellulose, polyvinyl pyrrolidone, as well as starches, modified starches, such as partially hydrolyzed starch, e.g., maltodextrin, saccharides, gelatin, natural or synthetic gums, and the like, as known in the art.

As described above, in some embodiments, a gastro-resistant material is included as a gastro-resistant binder and/or as a gastro-resistant outer coating. The material that makes up the gastro-resistant binder or outer coating serves the function of delaying the release of zinc salt and γ-PGA from the dosage form until it passes through the stomach and enters the intestine. When a gastro-resistant binder or coating is used, it may be used in combination with other (non-gastro-resistant) binders or coatings.

Generally, a gastro-resistant material is a matrix or polymer or other barrier that does not appreciably dissolve or swell in the acidic environment (pH ~3) of the stomach, but will dissolve or swell enough that the contents are released in the neutral to slightly alkaline environment (pH 7-9) of the intestine. Enteric coatings and enteric binders are examples of a gastro-resistant material.

Examples of gastro-resistant materials include cellulose acetate phthalate, cellulose acetate succinate, cellulose acetate trimellitate, hydroxypropylmethylcellulose-phthalate, a copolymer of two or more monomers selected from (i) an acrylate ester, (ii) a methylacrylate ester, and (iii) methacrylic acid, polyvinyl acetate phthalate, hypromellose acetate succinate, hypromellose phthalate, sodium alginate, shellac, and zein.

Numerous grades and pharmacopeial standards exist for gastro-resistant materials, and they provide a useful guide to selecting a suitable material for providing the function of delivering zinc and γ-PGA to the intestine. By controlling the coating thickness and polymer composition in an outer coating, or the amount of binder and the polymer composition, the release point can be adjusted to occur earlier or later, or within certain approximate regions of the intestine. Examples of the degree of control that can be achieved can be found in the line of methacrylic acid co-polymers available from Corel Pharma Chem (India) under the trade name Acrycoat® that meet various pharmacopeial standards, such as: USP/NF methacrylic acid copolymer, type A-NF, used at 4-5% and typically delivers the dosage form contents to the jejunum; USP/NF methacrylic acid copolymer, type C-NF, used at 4-5% and typically delivers the dosage form contents to the duodenum; and USP/NF methacrylic acid copolymer, type B-NF, used at 10-20% and typically delivers the dosage form contents to the colon. The latter (type B-NF) achieves the delivery with a pH-dependent polymer, though pH-independent polymers also can be used for delivery to the colon or the intestine as well.

Disintegrants include, without limitation, carmellose, carmellose sodium, croscarmellose sodium, crospovidone, alginates, low substituted hydroxypropyl cellulose, hydroxypropyl starch, partially pregelatinized starch, and the like, as known in the art.

Glidants include, without limitation, silicas, silicates, talc, calcium phosphate, and the like, as known in the art.

Lubricants include, without limitation, alkali metal or alkaline earth metal stearates, oleates, benzoates, acetates, chlorides, and the like, as known in the art.

Other types of excipients, such as buffers, preservatives, anti-oxidants, flavoring agents, sweeteners, coloring agents, are well-known and persons of ordinary skill in the art can readily select and apply such components to the formulations.

Solid dosage formulations may also be prepared to include NF-κB inhibitors. In embodiments that do not include such NF-κB inhibitors in the solid formulation, the NF-κB inhibitor may be co-administered using any other suitable formulation and form of administration.

Other types of active ingredients, such as vitamins, minerals, nutrients, and other nutritional or dietary supplements that are amenable to absorption in the intestine may also be added to the liquid or solid compositions and formulations described herein without departing from the scope of the invention, unless stated otherwise.

The compositions and formulations described herein may alternatively comprise, consist of, or consist essentially of zinc salt(s) and γ-PGA carrier and a gastro-resistant outer coating and/or a gastro-resistant binder, so long as it is consistent with the specification. The compositions and formulations may also lack or be substantially free of any component(s), e.g. active ingredient and/or excipient found in a prior art composition or that are otherwise not necessary to the disclosed invention.

Methods of Preparing Solid Dosage Forms

The zinc salts and γ-PGA, and the selected excipients may be sized, declumped, or powderized individually or in combination. The various components may be combined by dry mixing, or granulated by wet or dry granulation, spray, extrusion, rolling, or fluidized bed granulation, and thereafter may optionally be milled, or other such techniques as known in the art.

In some embodiments, zinc salt(s) and a γ-PGA carrier (unmodified γ-PGA and/or any forms of modified γ-PGA, as described above) may be prepared as a ZnPGA complex. Generally, the zinc salt(s) and γ-PGA carrier are combined and purified as described, for example, in Examples 1 and 2. For convenience, the solution of the obtained ZnPGA complex may be substantially dried and used as a dry or substantially powder in the procedure for prepared a solid dosage form.

The method for preparing solid dosage forms involves mixing together the desired amounts of (i) zinc salt(s) and γ-PGA carrier and/or (ii) a ZnPGA complex, and the excipients, which comprise one or more filler and/or one or more binder and/or one or more disintegrant and/or one or more lubricating agent and/or one or more glidant. As described above, in some embodiments, said one or more binder may be a gastro-resistant binder, and it may be used in combination with other (non-gastro-resistant) binders. When a granulating step is included, then any of the excipients may be added, in whole or in part, before, during, or after the granulating step. In some embodiments some or all of a lubricating agent are mixed in after a granulating step. In some of these embodiments, a glidant is also mixed in after the granulating step.

Where the granulation step involves using a solvent, such as water, or an organic solvent, or an aqueous organic solution to wet the blend of components as they are granulated, the resulting product is usually dried to remove residual solvent. Examples of organic solvents include ethanol and isopropanol, and the like, as known in the art. Preferably, substantially all of an organic solvent is removed in a drying step. When water is part of the solvent used in a granulation step, preferably no more than 10 wt %, or no more than 5 wt %, or no more than 2 wt % of the water is left after drying and proceeding to the next step.

The mixed or granulated solids may be formed into tablets by tableting the solids using compression, compaction, or molding. Thereafter, in some embodiments, the tablets are coated with a gastro-resistant coating, as described above. Generally, the gastro-resistant substance and, optionally, other excipients (e.g., plasticizer, emulsifier are dissolved or dispersed into an aqueous or organic solvent and then applied using any of numerous methods known in art, including spray coating, fluidized bed coating, pan coating, and the like. In some embodiments, the tablets are coated for purposes of appearance, mechanical stability, chemical stability, and the like, but without a gastro-resistant material included in the coating.

Alternatively, the mixed or granulated solids may be filled into a capsule or caplet, and enclosed inside. The term capsule includes soft capsules, hard capsules, gelcaps, vegetable capsules, and may be one-piece or two-piece capsules. Enterically-coated capsules are available (e.g., enteric capsule drug delivery technology), or the capsules may filled, enclosed, and then coated with the gastro-resistant coating by the methods mentioned above using a solution or dispersion of the substance, optionally with other excipients. In other embodiments, the mixed or granulated solids comprise a gastro-resistant binder material, and such solids can be loaded in capsules with or without an enteric coating.

The size and shape of either tablets or capsules is not particularly limited. It is expected that the desired dosage amounts of zinc salts and γ-PGA can be formulated into a tablet or capsule that is not unduly large.

Exemplary methods for preparing tablet dosage forms according to embodiments of the invention are provided below in Examples 11 and 12.

Dosing and Administration

The dosage forms described herein may be administered to provide a therapeutically effective amount of zinc to achieve the desired biological response in a subject. A therapeutically effective amount means that the amount of zinc delivered to the patient in need of treatment through the combined effects of the Zn, the γ-PGA, and any modifications to the γ-PGA, the form of any ZnPGA complex, the presence or absence of an NF-κB inhibitor, and/or the delivery efficiency of the dosage form, and the like, will achieve the desired biological response.

The desired biological response include the prevention of the onset or development of a tumor or cancer, the partial or total prevention, delay, or inhibition of the progression of a tumor or cancer, or the prevention, delay, or inhibition of the recurrence of a tumor or cancer in the subject, such as a mammal, such as in a human (also may be referred to as a patient).

All tumor types that are susceptible to PARP1-mediated necrosis are contemplated to be indications that can be treated according to the methods of treatment disclosed herein. Examples 4, 5 and 6 demonstrate the efficacy of treatments according to embodiments of the disclosed methods using embodiments of the disclosed compositions and pharmaceutical formulations. The results demonstrate effective treatments in mouse cancer cells and in human cancer cells in vivo, and in human subjects.

Achieving a therapeutically effective amount will depend on the formulation's characteristics, any will vary by gender, age, condition, and genetic makeup of each individual. Individuals with inadequate zinc due to, for example, genetic causes or other causes of malabsorption or severe dietary restriction may require a different amount for therapeutic effect compared to those with generally adequate levels of zinc.

The subject is generally administered an amount of zinc from about 1 mg up to about 300 mg zinc per day. For example about 25 mg, or 50 mg, or 75 mg, or 100 mg, or 150 mg, or 200 mg zinc per day. Multiple dosage forms may be taken together or separately in the day. The oral dosage forms generally may be administered without regard to meal time. Treatment generally continues until the desired therapeutic effect is achieved. Low dosage levels of the compositions and formulations described herein may also be continued as a treatment according to an embodiment of the invention if a tumor regresses or is inhibiting, for the purpose of preventing, delaying, or inhibiting its recurrence, or used as a preventative treatment.

EXAMPLES

Example 1: Preparation and Characterization of ZnPGA at pH 7.0 Using Phosphate-Precipitation Method for Removing Non-Bound Excess Zinc To prepare ZnPGA, 55 mg γ-PGA (50,000 Da molecular weight) was dissolved in 5 mL 10 mM MES buffer, pH 7.0, containing 10 mM $ZnSO_4$ at room temperature, and then sonicated while placed on ice for 10 minutes. Then, 0.5 mL 200 mM phosphate buffer, pH 7.0, was added to the solution to precipitate free zinc ions, and the mixture was filtered through a 0.2 μm syringe sterilization filter. The zinc content was measured using ICP-MS and by 4-(2-pyridylazo)-resorcinol assay. The final stock ZnPGA contained 1% (wt/vol) PGA and 400 μg/mL bound zinc ions. Stock ZnPGA solutions were prepared fresh on each day of administration.

Example 2: Preparation and Characterization of ZnPGA at pH 7.0 Using Dialysis Method for Removing Non-Bound Excess Zinc To prepare ZnPGA, 55 mg γ-PGA (50,000 Da molecular weight) was dissolved in 5 mL 10 mM MES buffer, pH 7.0, containing 10 mM $ZnSO_4$ at room temperature, and then sonicated while placed on ice for 10 minutes. Then, the solution was dialyzed on ice against 1 L 10 mM MES, pH 7.0, for 2 hours, successively three times, for a total of 3 volumes over 6 hours. The recovered solution was filtered through a 0.2 μm syringe sterilization filter. The zinc content was measured using ICP-MS and by 4-(2-pyridylazo)-resorcinol assay. The final stock ZnPGA contained 0.9% (wt/vol) PGA and 380 μg/mL bound zinc ions. Stock ZnPGA solutions were prepared fresh on each day of administration.

Example 3: In Vitro Flow Cytometric Analysis (FACS) of ZnPGA-Induced Cell Death in Human Cancer Cells with Different Drug Resistance Genotypes The mode of cell death induced by ZnPGA, whether apoptosis or necrosis, was examined in three human cancer cell lines with different drug resistance genotypes: H460 lung cancer (WT p53 apoptosis gene with no reported drug resistance), T98G neuroblastoma (mutated p53 and multidrug resistance protein 1 "MRP1" expression), and MES-SA Dx5 sarcoma (WT p53 and P-glycoprotein "PgP" multidrug resistance protein expression). Briefly, each cell line was prepared into 10,000 monolayer adherent state in late exponential growth phase per ATCC-suggested methods and media (RPMI-1640, F-12K, McCoy's 5A, EMEM, DMEM, etc), supplemented with 10% fetal bovine serum (FBS) and 1% penicillin/streptomycin in a $CO_2$ incubator at 37° C. and 5% $CO_2$ using 96-well plates with a medium volume of 200 μL per well. The prepared cells on the 96-well plates were treated with different concentrations of ZnPGA for 24 hours, followed by FACS characterization of the cell state.

Briefly, cells in each well of 96-well plates were harvested into microcentrifuge tubes and washed in 100 μL cold phosphate-buffered saline (PBS), pH 7.4. Next, each sample was centrifuged and resuspended in cold 100 μL binding buffer (10 mM HEPES, 140 mM NaCl, 2 mM $CaCl_2$ at pH 7.4). For staining, 5 μL AlexaFlour 488® annexin V (Annexin V: Cat #A13200, Invitrogen) and 5 μL of 100 μg/mL propidium iodide (PI) in binding buffer were added to each for staining at room temperature for 15 min. At the end of the incubation, the samples were placed on ice after adding 400 μL binding buffer to each sample until immediate FACS reading. FACS was performed with an excitation wavelength at 488 nm and reading the absorbance signals at 530 nm and 575 nm, at a 100 μL/min flow-rate.

Figure 2:
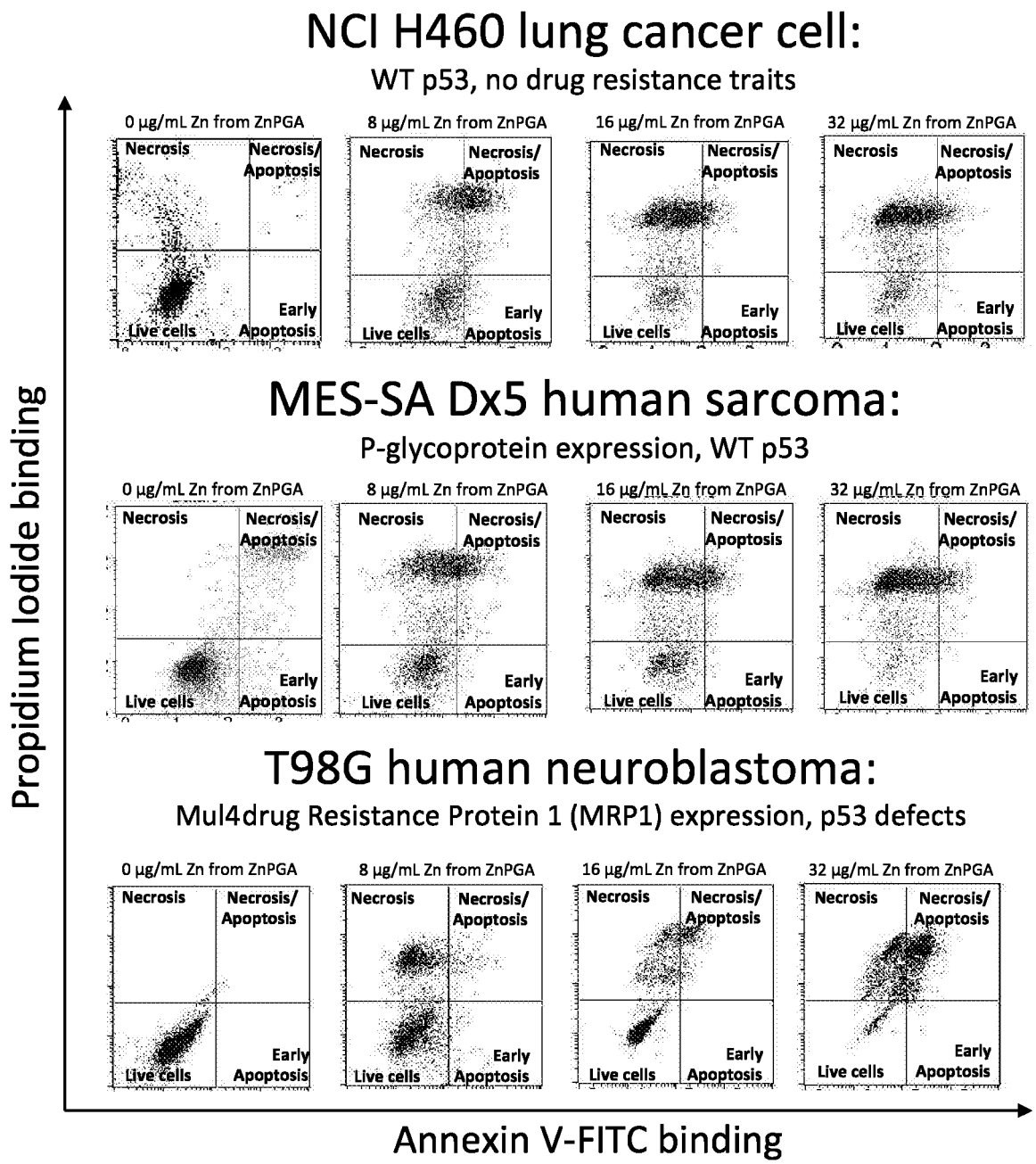
FIG. 2 shows the results of an in vitro flow cytometric analysis of human cancer lines treated with one embodiment of a ZnPGA composition.

The results are shown in FIG. 2, which shows in vitro cell-state quadrant analyses on the Annexin V and PI binding to the treated cells. The data demonstrated that ZnPGA dose-dependently and consistently induced necrotic cell death in all three cell lines with three different drug resistance genotypes after the 24 hour exposure. In FIG. 2, the upper panels show results from the treatment of non-resistant H460 human lung cancer cells (WT p53 and no drug resistance protein expression), the middle panels show a multidrug resistant MES-SA Dx5 human sarcoma (WT p53 and PgP multidrug resistance protein expression), and the lower panels show a multidrug resistant T98G human neuroblastoma (mutated p53 and MRP1 multidrug resistance protein expression). The dose of ZnPGA increases across each row in the figure.

Example 4: In Vivo Growth-Inhibition Effect of Orally Supplemented ZnPGA Against LL2 Murine Lung Cancer in the Lungs of Immunocompetent C57BL Allograft Model A monodisperse suspension of murine lewis lung carcinoma (LL2) cells were obtained by trypsinization of its in vitro culture and prepared in cold PBS at $2\times10^5$ cell/mL. A 0.5 mL suspension of LL2 cells was injected through the tail veins of C57BL/6 female mice, and the injected mice were sacrificed 16 days later for observation of pulmonary tumor growth. Oral drug treatment was started the day after tumor injection via dilution into the drinking water at the indicated doses. The animals were sacrificed 16 days after the cancer injection, and their lungs were observed for the growth of LL2 tumors.

Figure 3:
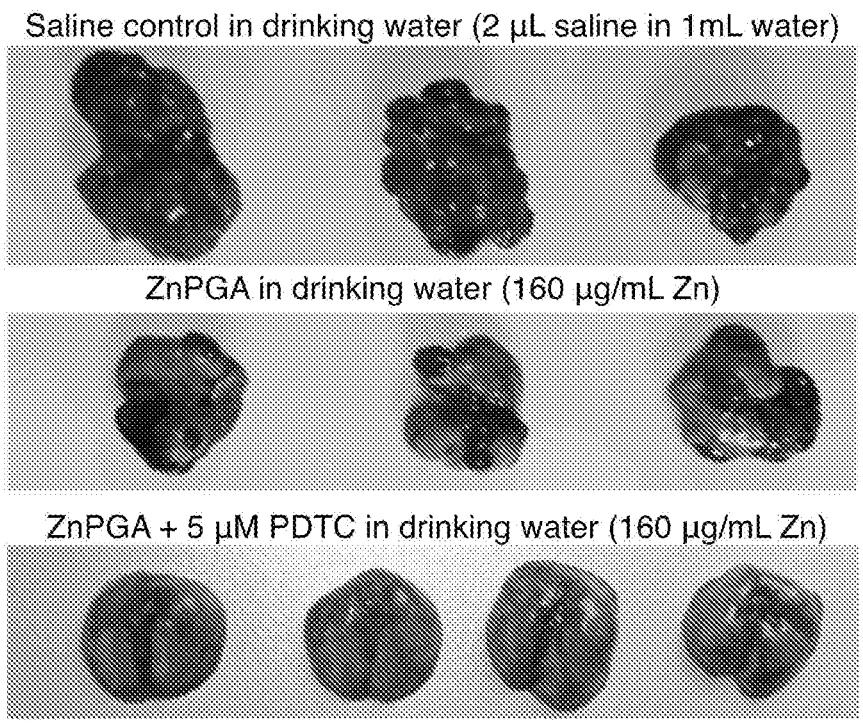
FIG. 3 shows the results of treating LL2 murine lung cancer allografts with embodiments of ZnPGA compositions.

FIG. 3 shows that doses of 160 µg/mL zinc in drinking water via ZnPGA over 15 days of treatment led to marked reduction of visibly solid LL2 tumor growth. Furthermore, supplementing the ZnPGA solution with the NF-kB inhibitor PDTC virtually eliminated the LL2 tumor growth in the orthotopic allograft model of murine lung cancer, suggesting a particular synergy between the NF-kB inhibitor PDTC and ZnPGA in their antitumor effects.

Example 5: In Vivo Growth-Inhibition Effect of Orally Supplemented ZnPGA Against H460 Human Lung Cancer in Immuno-Incompetent Athymic Nu/Nu Female Mice Subcutaneous Xenograft Model H460 single-cell suspension was prepared by trypsinization of its in vitro culture at logarithmic growth phase and prepared in serum-free cold RPMI-16040 medium at $10^7$ cells/mL. Subcutaneous xenografts of the human tumor on immuno-incompetent athymic Nu/Nu female mice were created by subcutaneously injecting 0.1 mL of the H460 cell suspension in the skin near the right flank of the mice. Oral drug treatment was started on the day following tumor injection. One group of three subjects received saline in drinking water, a second group of three subjects received cisplatin (5 mg/kg) intraperitoneally once weekly, and a third group of three subjects received ZnPGA (160 µg/mL zinc) via drinking water. Starting 14 day post-injection, the long and short dimensions of palpable tumor mass (length and width, respectively) were measured every two days using a digital caliper. The experiment continued for 28 days. The tumor volume was obtained by the formula, $V = \text{length} \times \text{width}^2 \times \frac{1}{2}$.

Figure 4:
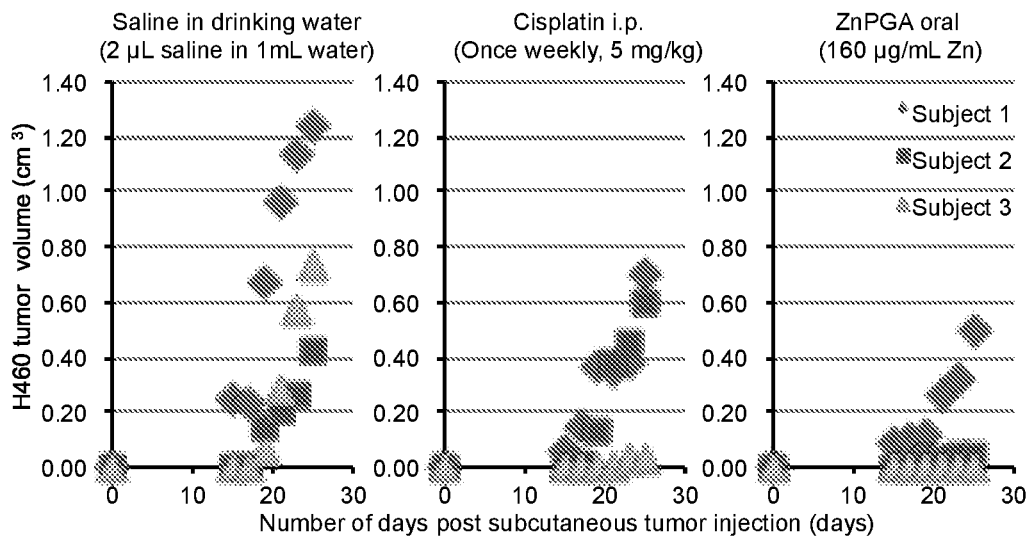
FIG. 4 shows the results of treating subcutaneous xenografts of H460 human lung cancer in mice with an embodiment of a ZnPGA composition.

FIG. 4 shows the results of the experiment. Consistent with the in vitro and the allograft orthotopic LL2 lung cancer model study results in C57BL mice of Examples 3 and 4, respectively, administering 160 µg/mL zinc in drinking water via ZnPGA led to marked inhibitory effects on the growth of subcutaneously xenografted H460 human lung cancer. Importantly, the tumor-suppressive effect of the orally supplemented ZnPGA was similar or better than those of the intraperitoneally injected cisplatin.

The foregoing invention having been described in detail and by way of example and illustration, those of skill in the art will appreciate the range of compositions and methods disclosed herein and embraced by the claims.

Example 6: Clinical Observations of Patients Receiving Granularized Mixture of Zinc(II) Salt and γ-Polyglutamic Acid Oral administration of a supplement-grade enteric-release coated tablet formulation made from granulized zinc sulfate and γ-polyglutamic acid mixture lead to (1) clinical regression of third drug-refractory early gastric cancer in a female patient with two previous histories of cancer, and (2) clinical regression of first primary early gastric cancer in a male patient without previous treatment or disease history. À

Example 7: Liquid Formulation

The composition of an exemplary embodiment of liquid formulation suitable for, e.g., injection comprises a zinc(II) salt, γ-PGA, sodium chloride, and water. The composition is prepared by combining zinc sulfate heptahydrate, γ-PGA (potassium salt, ≤100 kDa), sodium chloride and adding water to volume, wherein the concentrations of each component are 1 mg/mL zinc(II), 10 mg/mL γ-PGA, and 6.5 mg/mL sodium chloride. The resulting composition of approximately 276 mOsm/kg osmolality and pH 5.68 is suitable for injection in human patients.

Example 8: In Vitro Cell Survival Assay Upon Treatment with Zn(II)/γ-PGA Solution, Varying Zn(II) Concentration and γ-PGA Polymer Size A. Preparation of Zn/γ-PGA solution. γ-PGA, potassium salt (Xi'an Lyphar Biotech Co., Ltd., Xi'an, China), molecular weight≤100 kDa, was procured and samples were fragmented to various sizes by heating at 353 K in a pH 3 buffered aqueous solution for 1, 2, 6, 12, and 96 hr to produce increasingly smaller fragments of γ-PGA. The average molecular for the fragmented polymer was reported to be 50.1 kDa, 28.2 kDa, 15.9 kDa, 7.9 kDa, and 2.5 kDa, respectively. Peng, M., Liu, W., Chen, Q., and Hansen. E. W. (2010). Degradation rate of γ-polyglutamic acid probed by $^1$H-NMR spectral analysis and by PFGSTE NMR—internal consistency. *Int'l J. Research and Reviews in Applied Sciences* 3, 233-241. Zn/γ-PGA solutions were prepared at three concentrations of Zn(II) with each of the unfragmented polymer and the five fragmented polymers as follows. The γ-PGA was dissolved in water, Tris-HCl was added and the solution was buffered at pH 7.0, and then $ZnSO_4 \cdot 7H_2O$ was added to produce solutions with a zinc(ii) concentration of 1 µg/mL, 10 µg/mL, and 100 µg/mL, wherein the zinc: glutamate monomer ratio was 1:8. These solutions were used in the MTT cellular survival assays described next.

B. MTT assay. The effects of Zn/γ-PGA on cell viability for HeLa and MCF7 cells were determined using the MTT [3-(4,5-dimethylthiazol-2-yl)-2,5-diphenyltetrazolium bromide] assay. Briefly, cultured cells (see below) at a density of $4 \times 10^4$ cells/well were dispensed into a 96-well plate. Various concentrations of Zn/γ-PGA (6 γ-PGA polymer sizes, each at three concentrations of Zn(II)) were added (each condition was run in quadruplicate (N=4)), and, after incubation for 24 hr the well contents were centrifuged to collect the cells and the medium was removed. MTT solution (150 µL of 1 mg/mL working solution) was added to each well, incubated for 3 hr to permit crystal formazan development, and centrifuged to collect cells and crystal formazan. Cell viability was determined by dissolving the formed crystal formazan in 200 µL DMSO and measuring the optical absorbance at 540 nm.

C. Cell culture. HeLa and MCF7 cells were cultured in 96-well cell culture plates in 200 iµL Dulbecco's Modified Eagle's medium (DMEM) and (RPMI) containing 10% fetal bovine serum (FBS) and 1% antibiotics at 37° C. under a humidified atmosphere of 95% air and 5.0% $CO_2$ for 24 h.

Figure 5A:
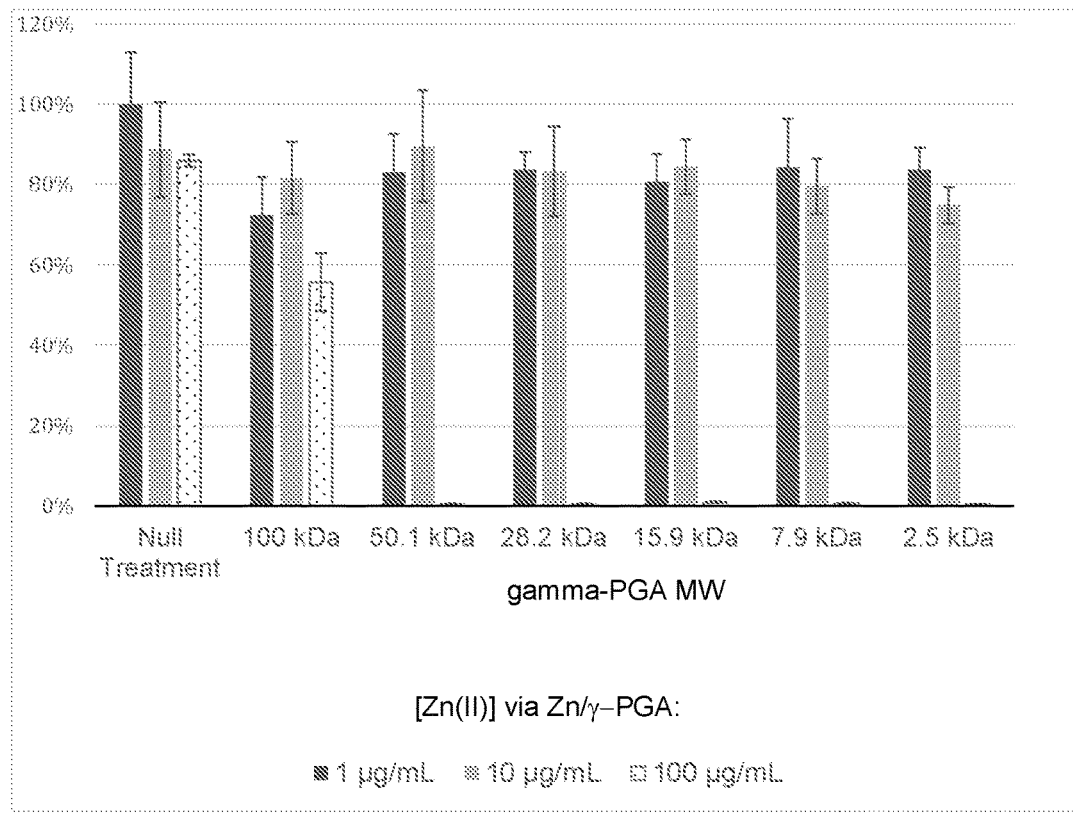
FIGS. 5A and 5B show the results of treating HeLa cells and MCF7 cells, respectively, with Zn(II)/γ-PGA compositions.
Figure 5B:
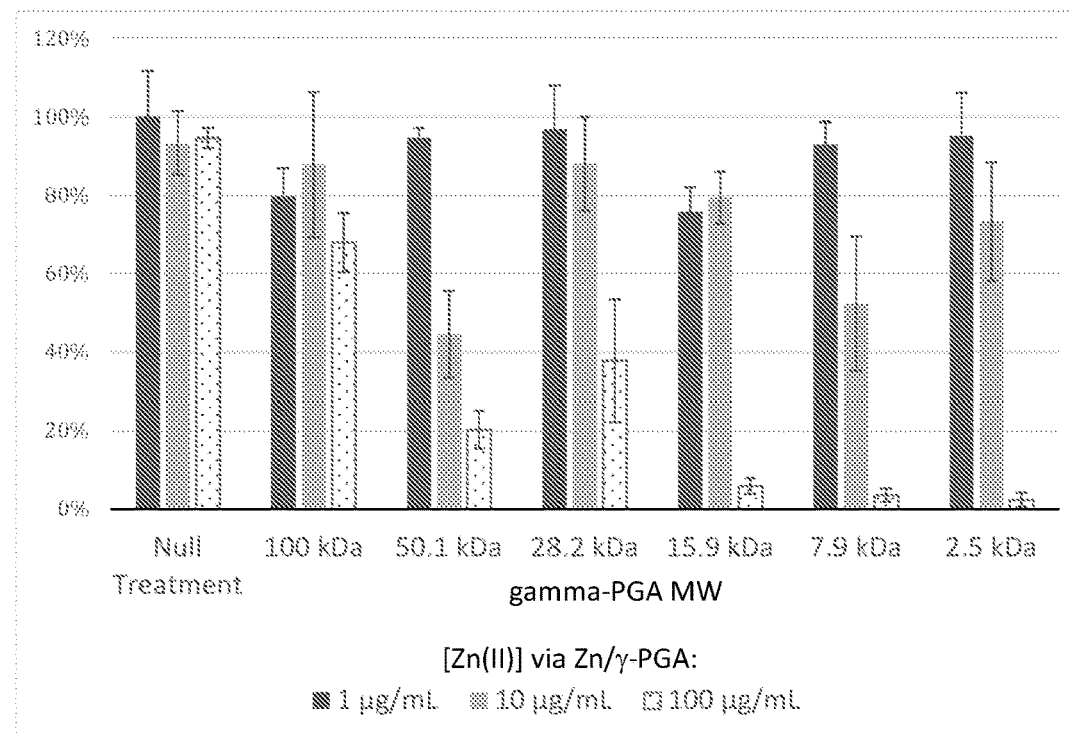

D. Assay results. The assay results are shown in FIGS. 5A and 5B for HeLa cells and MCF7 cells, respectively. From the results it is evident Zn/γ-PGA is cytotoxic and the effect increases with increasing Zn(II) concentration and decreasing size of the γ-PGA polymer.

Example 9: In Vitro Cell Survival Assay Upon Treatment with Zn(II)/γ-PGA Solution, Varying Zn(II) Concentration, 100 kDa γ-PGA Polymer, for Four Cell Types A. Preparation of Zn/γ-PGA solution. Zn/γ-PGA solutions were prepared as described in Example 8, using γ-PGA, potassium salt (Xi'an Lyphar Biotech Co., Ltd., Xi'an, China), polydisperse, molecular weight 45 kDa, to prepare solutions with a zinc(ii) concentration of 1.5625, 3.125, 6.25, 12.5, 25, 50, and 100 μg/mL, wherein the zinc:glutamate monomer ratio was 1:8.

B. MTT assay. The effects of Zn/γ-PGA on cell viability of HEK-293, HeLa, MCF7, and A549 cells were determined using the MTT assay as described in Example 8.

C. Cell culture. The cell culture conditions were the same as those described in Example 8.

Figure 6:
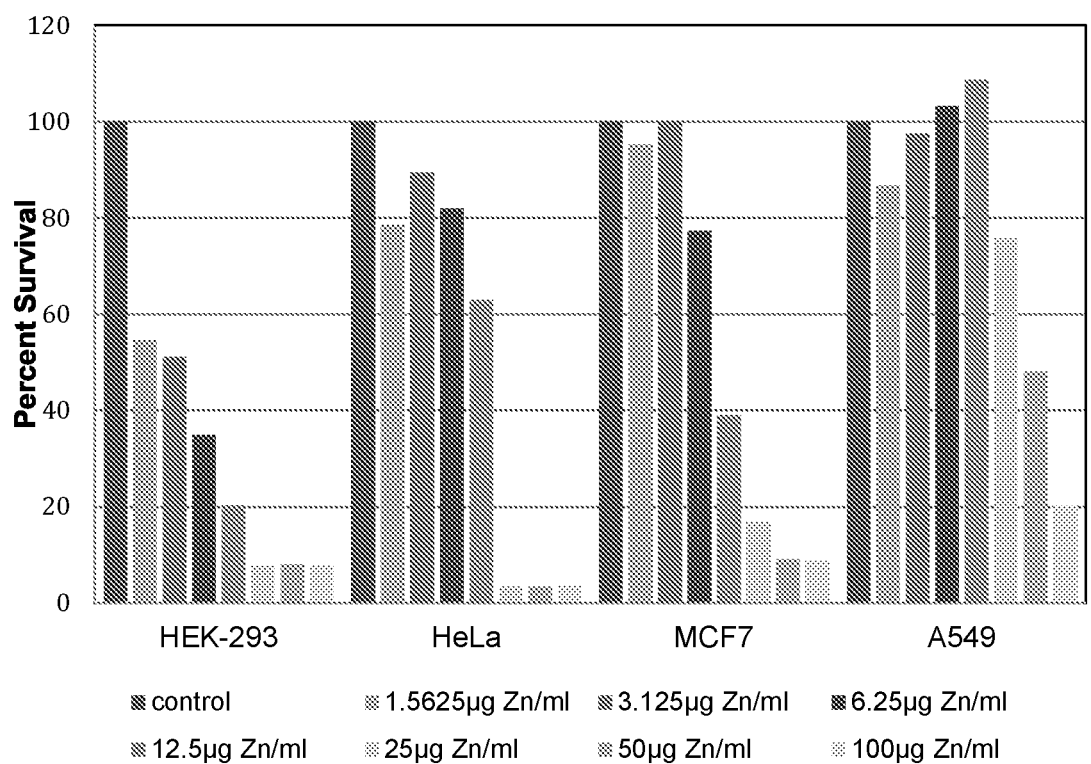
FIG. 6 shows the results of treating HEK-293 cells, HeLa cells, MCF7 cells, and A549 cells with Zn(II)/γ-PGA compositions.

D. Assay results. The assay results are shown in FIG. 6. From the results it is evident Zn/γ-PGA is cytotoxic and the effect increases with increasing Zn(II) concentration for the 45 kDa γ-PGA polymer.

Example 10: γ-Polyglutamic Acid-Zinc Liquid Composition

A composition useful for performing the invention according to an embodiment is shown in Table 1. The composition provides 0.68 mg of Zn ($Zn^{2+}$ ion) per 100 g as a liquid suspension formulation comprising wax-coated particles. A method for preparing the formulation follows the table. This composition is merely illustrative of one of many compositions useful for the subject invention.

TABLE 1

|  | Amount |  |
|---|---|---|
| Suspended Solid Components |  |  |
| Zinc sulfate•7H2O | 3.011 | mg |
| γ-PGA (MW($M_n$) ≤ 100 kDa) | 6.848 | mg |
| Sucrose | 9.5107 | g |
| HPMC-P | 0.3804 | g |
| Wax | 98.91 | mg |
| SUBTOTAL | 10 | g |
| Solution Components |  |  |
| Xanthan gum | 0.3 | g |
| Guar gum | 0.3 | g |
| Xylitol | 10 | g |
| Citric acid | 0.5 | g |
| Limonene | 0.1 | g |
| Potassium sorbate | 0.025 | g |
| Water | 78.7 | mL |
| TOTAL | 99.925 | g |

A. Preparation of coated ZnPGA microspheres (cZPM). 200 mL water containing 10 g sucrose (5% w/v), 45 mg γ-PGA, and 19.79 mg zinc sulfate heptahydrate (4.5 mg as elemental Zn) was prepared and freeze-dried. The resulting powder was then triturated in a 1:4 ratio with finely divided sucrose containing up to 5% cornstarch and pressed through a No. 50 U.S. Standard stainless steel sieve (48 Mesh). This powder was then suspended in 200 mL of white paraffin oil in a 400 mL beaker. The mixture was dispersed by stirring at 260 rpm with a 44 mm polyethylene three-blade paddle fitted to a high-torque stirrer (Type RXR1, Caframo, Wiarton, Ontario). To the suspension was added 20 mL of 10% (w/v) hydroxypropylmethylcellulose-phthalate (HPMC-P) in acetone-95% ethanol (9:1). Stirring was continued for 5 min, whereby microspheres form, and then 75 mL of chloroform was added. The suspending medium was decanted, and the microspheres were briefly resuspended in 75 mL of chloroform, and air-dried at ambient temperature. Upon drying, the microspheres were coated with Carnauba wax. Specifically, 1 g of Carnauba wax was dissolved in 200 mL of white paraffin oil at 70° C., and cooled to less than 45° C. To this cooled wax-paraffin solution, the prepared microspheres were added and suspended for 15 mins with constant stirring. The wax solution was then decanted, and the microspheres were collected on filter paper to absorb the excess wax solution to obtain coated ZnPGA microspheres (cZPM).

B. Preparation of liquid suspension solution of coated ZnPGA microspheres (cZPM). The following components: 0.3 g xanthan gum (e.g., as a suspending polymer); 0.3 g guar gum (e.g., as a viscosity agent); 10 g xylitol (e.g., as a sweetener); 0.5 g citric buffer (e.g., as a buffer); 0.1 g limonene (e.g., as a flavoring agent); 0.025 g potassium sorbate (e.g., as a preservative), were dissolved in 78.7 mL water. The pH of the aqueous solution was adjusted to pH 4.5, and then 10 g cZPM was suspended in the aqueous solution to obtain the cZPM liquid suspension.

Example 11: γ-Polyglutamic Acid-Zinc Composition

A composition useful for performing the invention according to an embodiment is shown in Table 2. The composition provides 25 mg of Zn ($Zn^{2+}$ ion) per tablet. A method for preparing the tablet follows the table. This composition is merely illustrative of one of many compositions useful for the subject invention.

TABLE 2

| Component | Amount per tablet | Weight % |
|---|---|---|
| Zinc sulfate | 110 mg | 22% |
| γ-Polyglutamic acid | 110 mg | 22% |
| Microcrystalline cellulose | 100 mg | 20% |
| Starch | 85 mg | 17% |
| Silicon dioxide | 50 mg | 10% |
| Magnesium stearate | 25 mg | 5% |
| Cellulose acetate phthalate | 20 mg | 4% |
| Total | 500 mg | 100% |

Coated tablets with the composition shown in Table 2 may be prepared using a wet granulation technique. First, zinc sulfate and γ-polyglutamic acid are mixed together dry. Microcrystalline cellulose, starch, and silicon dioxide are further added, and the dry components are all further mixed together. The mixed components are transferred to a granulator and an appropriate amount of aqueous ethanol is added and granulation is carried out. The obtained granulated mixture is dried at 50-70° C. to yield a granulated composition with less than about 5% water content. Magnesium stearate is added to and mixed with the granulated composition. The obtained mixture is compressed into tablets. Finally, the tablets are coated with cellulose acetate phthalate using standard techniques, as known to those skilled in the art.

Example 12: γ-Polyglutamic Acid-Zinc Composition

A composition useful for performing the invention according to an embodiment is shown in Table 3. The composition provides 30 mg of Zn ($Zn^{2+}$ ion) per tablet. A method for preparing the tablet follows the table. This composition is merely illustrative of one of many compositions useful for the subject invention.

TABLE 3

| Component - Tablet core | Amount per tablet | Weight % |
|---|---|---|
| Zinc sulfate•7H2O | 132.3 mg | 26.5% |
| γ-PGA (MW(M$_n$) ≤ 100 kDa) | 132.3 mg | 26.5% |
| Microcrystalline cellulose | 102.5 mg | 20.5% |
| HPMC-P | 65.0 mg | 13% |
| Maltodextrin | 37.9 mg | 7.6% |
| Carboxymethylcellulose-Ca | 5.0 mg | 1.0% |
| Aerosil ® | 5.0 mg | 1.0% |
| Magnesium stearate | 5.0 mg | 1.0% |
| 70% Ethanol | q.s | NA* |
| Purified water | q.s | NA* |
| SUBTOTAL | 485 mg | |
| Component - Tablet coating | Amount | Weight % |
| HPMC-P | 10.0 mg | 2.0% |
| HPMC | 5.0 mg | 1.0% |
| Isopropyl alcohol | 0.16 mL | NA* |
| Purified water | 0.13 mL | NA* |
| TOTAL | 500 mg | 100% |

*It is assumed here that the solvents (ethanol, isopropyl alcohol, and water) are present in insignificant amounts in the formulated tablet.

Coated tablets with the composition shown in Table 3 may be prepared as follows. First, zinc sulfate, γ-polyglutamic acid, microcrystalline cellulose, HPMC-P (hydroxypropylmethylcellulose phthalate), maltodextrin, and carboxymethylcellulose-calcium were mixed together dry. The mixed components were transferred to a granulator and an appropriate amount of 70% aqueous ethanol was added and wet granulation was carried out. The obtained granulated mixture was dried at up to about 60° C. to yield a granulated composition with less than about 3% LOD (loss on drying). Silica (e.g., Aerosil®) and magnesium stearate was added to and mixed with the granulated composition. The obtained mixture was compressed into tablets. The tablets were first coated using an isopropyl alcohol solution of HPMC-P, and then coated in a second step using an aqueous solution of HPMC, using standard techniques, as known to those skilled in the art.

I claim:

1. A method of inducing PARP1-mediated tumor necrosis in a tumor in a patient, the method comprising administering a therapeutically effective amount of Zn(II) complexed to a carboxylate moiety of γ-polyglutamic acid in a γ-polyglutamic acid carrier in a dosage form to the patient with the tumor;
    wherein said tumor has a drug-resistant phenotype selected from dysfunctional p53, MDR1 overexpression, and MRP1 overexpression.

2. The method according to claim 1, wherein said Zn(II) complexed with said γ-polyglutamic acid carrier in said dosage form are administered in a therapeutic amount in combination with a therapeutic amount of a nuclear factor kappa B (NF-κB) inhibitor.

3. The method according to claim 1 or 2, wherein said dosage form is a solid dosage form or a liquid dosage form.

4. The method according to claim 3, wherein said dosage form is a solid dosage form, and is selected from a tablet, a minitab, a hard capsule, a soft capsule, a caplet, a gelcap, an oral disintegrating film, granules, pellets, a paste, and a powder sachet.

5. The method according to claim 3, wherein said dosage form is a liquid dosage form, and is selected from a liquid solution, a liquid suspension, a syrup, and an oral spray.

6. The method according to claim 3, wherein said administering step is selected from an oral administration and an injection administration.

* * * * *